(12) United States Patent
Baraldi

(10) Patent No.: US 7,112,607 B2
(45) Date of Patent: Sep. 26, 2006

(54) ALLOSTERIC ADENOSINE RECEPTOR MODULATORS

(75) Inventor: Pier Giovanni Baraldi, Ferrara (IT)

(73) Assignee: King Pharmaceuticals Research & Development, Inc., Cary, NC (US)

( * ) Notice: Subject to any disclaimer, the term of this patent is extended or adjusted under 35 U.S.C. 154(b) by 292 days.

(21) Appl. No.: 10/101,817

(22) Filed: Mar. 20, 2002

(65) Prior Publication Data

US 2002/0147185 A1 Oct. 10, 2002

Related U.S. Application Data

(60) Division of application No. 09/811,679, filed on Mar. 19, 2001, now Pat. No. 6,727,258, which is a continuation-in-part of application No. 09/156,077, filed on Sep. 17, 1998, now Pat. No. 6,323,214, which is a continuation-in-part of application No. 08/959,758, filed on Oct. 29, 1997, now Pat. No. 5,939,432.

(51) Int. Cl.
*A61P 29/00* (2006.01)
(52) U.S. Cl. .................................... 514/443
(58) Field of Classification Search ................ 514/443, 514/278, 324; 549/57, 49; 546/18, 202
See application file for complete search history.

(56) References Cited

U.S. PATENT DOCUMENTS

| | | | | |
|---|---|---|---|---|
| 3,558,606 | A | | 1/1971 | Tinney ..................... 260/239.3 |
| 4,256,755 | A | * | 3/1981 | Smith, Jr. ................... 514/377 |
| 5,026,698 | A | | 6/1991 | Fujikawa et al. ........... 514/215 |
| 5,532,233 | A | | 7/1996 | Weber et al. ................ 514/219 |
| 5,585,385 | A | | 12/1996 | Natsugari et al. ........... 514/300 |
| 5,593,988 | A | | 1/1997 | Tahara et al. ............... 514/219 |
| 5,747,486 | A | | 5/1998 | Sohda et al. ................ 514/211 |
| 5,939,432 | A | | 8/1999 | Baraldi ....................... 514/301 |
| 6,046,189 | A | | 4/2000 | Sohda et al. ........... 514/217.07 |
| 6,143,777 | A | * | 11/2000 | Jonas et al. ................. 514/447 |
| 6,177,444 | B1 | | 1/2001 | Baraldi |
| 6,194,449 | B1 | | 2/2001 | Baraldi ....................... 514/447 |
| 6,323,214 | B1 | | 11/2001 | Baraldi ....................... 514/301 |
| 6,713,638 | B1 | * | 3/2004 | Linden et al. ................. 549/57 |

FOREIGN PATENT DOCUMENTS

| | | | |
|---|---|---|---|
| DE | 2204735 | * | 8/1972 |
| DE | 2233457 | | 2/1973 |
| DE | 2323149 | | 11/1973 |
| DE | 3724031 | | 1/1998 |
| EP | 407955 | | 1/1991 |
| ES | 393101 | | 5/1974 |
| JP | 5345785 | | 12/1993 |
| JP | 50011397 | | 4/1995 |
| JP | 7304755 | | 11/1995 |
| JP | 8337583 | | 12/1996 |
| WO | 93/07129 | | 4/1993 |
| WO | 96/14319 | | 5/1996 |
| WO | WO99/21617 A2 | | 5/1999 |

OTHER PUBLICATIONS

WEBSTER'S Ninth New Collegiate Dictionary, (c) 1994 by Merriam-Webster Inc., p. 787.*
Amemiya, Y. et. al., "Synthesis of Thromboxane Synthetase Inhibitory Activity . . . , " J. Med. Chem., 1989, vol. 32, No. 6, pp. 1265-1272.*
Bruns, R.F. et. al., Chemical Abstract, vol. 114, Abstract #220744, 1991.*
Dray, A. "Inflammatory mediators of pain" Brit. J. of Anaes., 1995, vol. 75, pp. 125-131.*
Corral, et al., "Reacciones de Bischlery de Friedlander Con 2-Amino-3Aroil-Tiofenoes," Afinidad, Mar.—Apr. (1978).
Cas for Routh, et al., "Tachykinin Receptors in the Spinal Cord, Progress in Brain Research," vol. 104, pp. 93-108.
Cas for Chesselet, et al., "Ischemic Damage in the Striatum of Adult Gerbils: Relative Sparing of Somatostatinergic and Cholinergic Interneurons Contrasts with Loss of Efferent Neurons," Experimental Neurology, vol. 110, No. 2, pp. 209-218.
Cas for Cragg, et al., Tachykinin Antagonists in Cartoid Body Responses to Hypoxia and Substance P in the Rat, Respiration Physiology, vol. 95, No. pp. 295-310.
Cas for Benedek, et al., "Potentiation of Thermoregulatory and Analgesic Effects of Morphine by Calcium Antagonists," Pharmacological Research Comms., vol. 16, No. 10, pp. 1009-1018.
Cas for Ghio, et., "Clinical Evaluation of Calcium-Antagonist Drugs," J of Cardiovascular Pharmacology, vol. 20, pp. S71-74.
Cas for Zhou, et al., "Effects of Calcium Blockers on the Performance of Left and Right Ventricles During Acute Hypoxia," Sheng Li Hseuh Pao, vol. 44, pp. 237-243.

(Continued)

*Primary Examiner*—Bruck Kifle
(74) *Attorney, Agent, or Firm*—Jones Day; Paivi Kukkola

(57) ABSTRACT

The present invention relates to compounds of formula (IA):

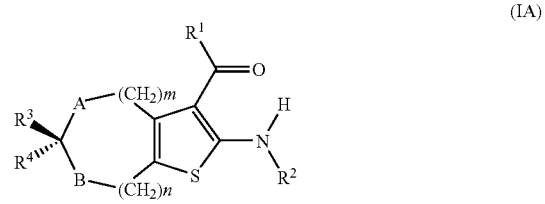

(IA)

the preparation thereof, pharmaceutical formulations thereof, and their use in medicine as allosteric adenosine receptor modulators for uses including protection against hypoxia and ischemia induced injury and treatment of adenosine-sensitive cardiac arrhythmias.

8 Claims, No Drawings

OTHER PUBLICATIONS

Cas for Ueno, et al., "Simultaneous Determination of a New Dihydropyridine Calcium Blacker and its Pyridine Metabolite in Dog Plasma by Column Switching High-Performance Liquid Chromatography with Electrochemical and Ultravioletdetection," Analytical Science.

Kollias-Baker, et al., "Allosteric Enhancer PD 81,723 ACTS by Novel Mechanism to Potentiate Cardiac Actions of Adenosine," Cir. Research, vol. 75, No. 6, pp. 961-971 (1994).

Kollias-Baker, et al., "The Allosteric Enhancer, PD 81,723, Potentiates the Cardiac Effects of Adenosine by Enchancing the Binding of Agonists to A1 Adenosinereceptors," A Dissertation Presented to the Graduate School of the University of Florida (1994).

Leung, et al., "Enhancement of Adenosine A1 Receptor Functions by Benzoylthiophenes in Guinea Pig Tissues In Vitro," Archives of Pharmacology, vol. 352, No. 2, pp. 206-212.

Mizumura, et al., "PD 81,723 An Allosteric Enhancer of the A1 Adenosine Receptor, Lowers the Threshold for Ischemic Preconditioning in Dogs," Cir. Research, vol. 79, No. 3, pp. 415-423 (Sep. 1996).

Mudumbi, et al., "Cardia Functional Responses to Adenosine by PD 81,723, An Allosteric Enhancer of the Adenosine A1 Receptor," American Journal of Physiology, vol. 264, pp. H 1017-H1022.

Nakanishi, et al., "Studies on Pcychotropic Drugs, 18.1Synthesis and Structure-Activity Relationships of 5-Phenyl-1,3-Dihydro-2H-Thieno[2,3-E][1,4]Diazepin-2-Ones," Journal of Medicinial Chemistry, vol. 16, No. 3, pp. 214-219, 1973.

Robba, et al., "No. 144-Thienopyrimidines. IX—Etude de la Thieno[2,3-D]Pyrimidines et de ses Derives," Buletinede la Societe Chimique de France, pp. 761-764 (1976)-.

Amoah-Apraku, et al., "Selective Potentiation by An A1 Adenosine Receptor Enhancer of the Negative Dromotropic Action of Adenosine in the Guinea Pig Heart," No. 2, pp. 611-617 (1993).

Bhattacharya, et al., "Effects of Long-Term Treatment With the Allosteric Ehnancer, PD 81,723, N Chinese Hamster Ovary Cells Expressing Recombinant Human A1 Adenosine Receptors," Molecular Pharm., vol. 50, pp. 104-111 (1996).

Bhattacharya, et al., "The Allosteric Enhancer, PD 81,723, Stabilizez Human A1 Adenosine Receptor Coupling to G Proteins," Biochimica et Biophysics ACTA, 1265: pp. 15-21, 1995.

Bruns, et al., "Allosteric Enhancement of Adenosine A1 Receptor Binding and Function by 2-Amino-3-Benzoylthiophenes," Molecular Pharm., vol. 38, No. 6, pp. 939-949 (1990).

Bruns, et al., "Structure-Activity Relationships for Enhancement of Adenosine A1 Receptor Binding by 2-Amino-3-Benzoylthiophenes," Molecular Pharm., vol. pp. 950-958 (1990).

Cao, et al., Adenosine A1 Receptor Enhancer, "PD 81,723 and Cerebral Ischemia/Reperfusion Injury in th e Gerbil," General Pharmacology, vol. 26, No. 7, pp. 1545-1548 (1995).

Dennis, et al., "Modulation of Atrioventricular Nodal Function by Metabolic and Allosteric Regulators Endogenous Adenosine in Guinea Pig Heart," Circulation, vol. 94, No. 10, pp. 2551-2559 (1996).

Fortea, "Thieno[2,3-D]Pyrimidine3-Oxides. Synthesis and N-Oxide Reactions of 4-Phenyl-And-4-Aminotheino[2,3-,]Pyrimidine3-Oxides," Journal Fur Praktische Chemie, Band 317, Heft 5, p 705-711 (1975).

Hromatka, et al., Uber die Nitrierung von 7-Chlor-5-Phenyl-1H-Thieno[2,3-E]1,-4-Diazepin-2(3H)-on, Monatsheft fur Chemie, vol. 104, pp. 709-714 (1973).

Janusz, et al., "Fu nctional Activity of the Adenosine Binding Enhancer, PD 81,723, In the In Vitro Hippocampal Slice," Brain Research, vol. 567, pp. 181-187, (1991).

Kollias-Baker, et al., "Novel Approach for Enhancing Atrioventriuclar Nodal Conduction Delay Mediated by Endogenous Adenosine," Cir. Research, vol. 75, No. 6, pp. 972-980 (1994).

Copy of International Search Report, dated Aug. 6, 2003, issued in PCT/US02/08821 (filed Mar. 19, 2002).

Kollias-Baker, et al., Agonist-Independent Effect of an Allosteric Enhancer of the $A_1$ Adenosine Receptor in CHO Cells Stably Expressing the Recombinant Human A1 Receptor, *Journal of Pharmacology and Experimental Therapeutics*, 1997, 281, 761-768.

Van der Klein, et al, "Allosteric Modulation of the Adenosine A1 Receptor. Synthesis and Biological Evaluation of Novel 2-Amino-3-Benzoylthiophenes as Allosteric Enhancers of Agonist Binding," *J. Med. Chem*, Aug. 1999, 42, 3629-2635.

Tinney, et al., "Synthesis and Pharmacological Evaluation of 2,3-Dihydro-1H-thieno[2,3-e][1,4]diazepines," *J. Med. Chem*, 1974, 17, 624-630.

Baba, et al., "Studies on Disease-Modifying Antirheumatic Drugs. IV. Synthesis of Novel Thieno[2,3-b: 5,4-c]Dipyridine Derivatives and Their Anti-Inflammatory Effect," *Chem. Pharm. Bull.*, Jul. 1999, 47, Abstract.

Copy of International Search Report, dated May 28, 1999, issued in PCT/US98/20333 (filed Sep. 30, 1998).

Bruns, R.F., "Adenosine Receptors," *Ann. N.Y. Acad. Sci.* 1990, 603, 211-226.

Dave, K.G. et al., "Reaction of Nitriles under Acidic Conditions . . . ," *J. Heterocyclic Chemistry* 1980, 17, 1497-1500.

Amemiya et al., "Synthesis and Thromboxane Synthetase Inhibitory Activity of Di- or Tetrahydrobenzo[b]thiophene Carboxylic Acid Derivatives," *J. Med. Chem*. 1989, 32, 1265-1272.

Gungor, T. et al., ". . . Adenosine Receptor Agonists . . . as Potent Antinociceptive Agents", *J. Med. Chem.*, 1994, 37, 4307-4325.

Baraldi, P.G., et al., "Allosteric Modulators for the $A_1$ -Adenosine Receptor," *Expert Opin. Ther. Patents* 2004, 14, 71-79.

\* cited by examiner

ALLOSTERIC ADENOSINE RECEPTOR MODULATORS

REFERENCE TO OTHER APPLICATIONS

This application is a divisional patent application of U.S. patent application Ser. No. 09/811,679, filed Mar. 19, 2001 now U.S. Pat. No. 6,727,258. Application Ser. No. 09/811,679, is in turn, a continuation-in-part of U.S. patent application Ser. No. 09/156,077 filed Sep. 17, 1998 now U.S. Pat. No. 6,323,214 to Pier Giovanni Baraldi that is, in turn, a continuation-in-part of U.S. patent application Ser. No. 08/959,758 filed Oct. 29, 1997 now U.S. Pat. No. 5,939,432.

BACKGROUND OF THE INVENTION

The present invention relates to certain thiophene derivatives and their use in the practice of medicine as allosteric modulators of adenosine receptors.

Adenosine (Ado) is an autocoid (or local hormone) that modulates numerous functions in the cardiovascular and other organ systems. The actions of Ado are mediated by at least four subtypes of cell surface receptors called $A_1$, $A_{2a}$, $A_{2b}$, and $A_3$. Because the ubiquity of adenosine receptors (AdoRs) throughout the body of a human, their indiscriminate activation may cause undesirable side effects. Therefore, new drug design approaches to achieve receptor and organ selectivity are needed.

The overall function of Ado appears to be the regulation of the balance between oxygen (or energy) supply and consumption (or work). Ado increases oxygen supply by causing vasodilation and decreases oxygen consumption or work by inhibiting cellular functions, e.g., slowing of heart rate. Consistent with this protective function, $A_1$AdoR agonists, Ado uptake blockers and Ado deaminase inhibitors have been shown to reduce cellular damage and dysfunction during hypoxia and ischemia. This protective role of Ado and $A_1$AdoR agonists has been shown in heart, brain, liver, and intestines. This and other potentially beneficial actions of Ado have led to increased interest in the development of Ado-related drugs targeted to ameliorate conditions such as myocardial ischemia and stroke.

However, the widespread expression of Ado receptors and the lack of sufficiently selective adenosine agonists have been a major impediment to the successful development of direct-acting AdoR agonists to exploit the cytoprotective properties of Ado. Therefore, other pharmacological approaches such as allosteric modulators of Ado may prove to be a valuable alternative to direct-acting Ado agonists and nucleoside uptake blockers. Such agents should selectively modulate the response to Ado in only those organs or localized areas of a given organ in which production of Ado is increased. Thus, allosteric modulators of Ado function should provide a more selective therapeutic effect than direct-acting AdoR agonists. Their action will be limited to times and locations at which significant release of Ado occurs so that systemic side effects would largely be avoided.

Allosteric modulation of the actions of Ado on the $A_1$AdoR by several 2-amino-3-benzoylthiophenes on cultured cells, cardiac and brain preparations have been reported. The specificity of these compounds for $A_1$AdoRs have also been demonstrated.

A number of compounds known to modulate the action of neurotransmitters, hormones and peptides bind at sites distinct from, but functionally linked to, the primary recognition site of the respective receptors. This form of interaction between two different ligands at the same receptor protein, which may result in modulation in the form of enhancement or inhibition of each others binding and function, is referred to as allosterism. Positive (enhancement) or negative (inhibition) allosterism is an important mechanism of action of drugs. For example, allosteric interactions between the GABA receptor and benzodiazepines, to atrial natriuretic factor (ANF) receptor and amiloride, the dextromethorphan binding site and ropizine, and the muscarinic receptor and gallamine have been described.

The compounds of the present invention have been found to be potent, yet selective allosteric modulators of AdoR agonists, and in some cases, AdoR antagonists.

BRIEF SUMMARY OF THE INVENTION

Compounds useful as potent, yet selective allosteric modulators of adenosine receptors, with activity as AdoR agonists, and, in come cases AdoR antagonists, and methods of preparation and use thereof, are disclosed.

The compounds have the following general formulas IA and IB:

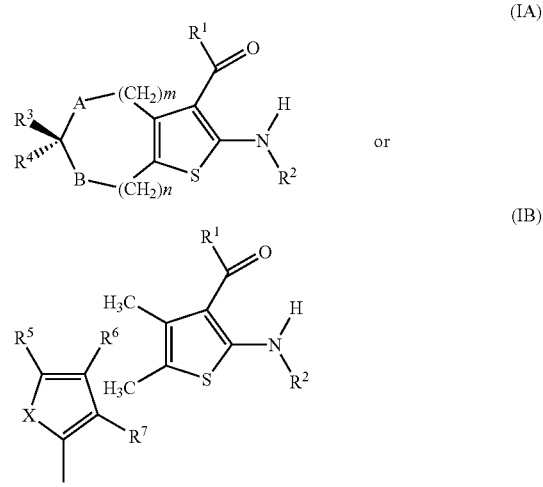

wherein:
R$^1$ is

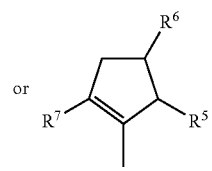

wherein R$^2$ is H, C(=O)R$^8$;
R$^8$ is H, alkyl, substituted alkyl, aralkyl, substituted aralkyl, aryl, or substituted aryl;
R$^3$ and R$^4$ are independently H, alkyl, substituted alkyl, aryl, substituted aryl, aralkyl, alkenyl, substituted alkenyl, alkynyl, substituted alkynyl, halogen, hydroxy, alkylsulfonyloxy, arylsulfonyloxy, substituted arylsulfonyloxy, alkoxy, alkylthio, or arylthio;
or if R$^3$ and R$^4$ are both alkoxy or alkylthio, may form a 1,3-dioxolan-2-yl, 1,3-dioxan-2-yl, 1,3-dithiolan-2-yl, or 1,3-dithian-2-yl group;

or together $R^3$ and $R^4$ may form a carbonyl oxygen;

$R^5$, $R^6$, and $R^7$ are independently H, alkyl, substituted alkyl, aryl, substituted aryl, halogen, hydroxy, nitro, amino, substituted amino, disubstituted amino, alkoxy, aryloxy, alkylthio, arylthio, sulfonamido, or substituted sulfonamido;

or together $R^5$ and $R^6$ or $R^6$ and $R^7$ may be CH=CH—CH=CH, such that they form a fused aromatic ring;

A and B are independently O, S, or N—$R^8$;

or A and B may independently represent a carbon-carbon single bond;

m and n are independently 0, 1, 2, or 3;

except that A and B cannot both represent a carbon-carbon single bond when m and n are both 0; and X is CH=CH, CH=N, N=CH, O, S, or N—$R^8$.

The compounds can be used in a method for cardioprotection, neuroprotection, pain management, reduction of free fatty acids, triglycerides, or glucose levels, adjunct therapy in diabetes, treatment of GI disorders, treatment of glaucoma; treatment of sleep disorders; treatment of cardiac disarrythmias (peroxysmal supraventricular tachycardia, treatment of congestive heart failure or treatment of inflammation.

The compounds can be used in a pharmaceutical formulation that includes a compounds of formulas IA or IB and one or more excipients. Various chemical intermediates can be used to prepare the compounds of formula IA or IB:

BRIEF DESCRIPTION OF THE DRAWINGS

Not applicable.

DETAILED DESCRIPTION OF THE INVENTION

The present application discloses compounds useful as potent, yet selective allosteric modulators of adenosine receptors, with activity as AdoR agonists, and in some cases, AdoR antagonists, and methods of preparation and use thereof.

The compounds can be used in a method for allosterically modulating adenosine receptors in a mammal, including a human. The methods involve administering an effective amount of a compound of formula IA or IB sufficient to moderate adenosine receptors to the mammal.

The compounds can be used in a pharmaceutical formulation that includes a compound of formula IA or IB and one or more excipients. Various chemical intermediates can be used to prepare the compounds of formula IA or IB.

As used herein the term "lower alkyl" means a monovalent radical, straight or branched chain, derived from the corresponding alkane having one to ten carbon atoms, i.e., methyl, ethyl, propyl, Isopropyl, n-butyl, sec-butyl, t-butyl, pentyl (all isomers), etc. Likewise, "lower alkylene" means a divalent radical of the corresponding alkane. Further, as used herein, other moieties having names derived from alkanes, such as alkoxyl, alkanoyl, alkenyl, cycloalkenyl, etc when modified by "lower," have carbon chains of ten or less carbon atoms. In those cases where the minimum number of carbons are greater than one, e.g., alkenyl (minimum of two carbons) and cycloalkyl, (minimum of three carbons), it is to be understood that "lower" means at least the minimum number of carbons.

As used herein the term "amino acid" means an alpha amino acid selected from those amino acids which naturally occur in proteins but without regard for specific stereochemical properties. The term "protected amino acid" means an amino acid of which the alpha amino group has been converted to a less reactive moiety, but a moiety which can be converted back to the amino group with relative ease. The terms "amino acid residue" and "amino acid moiety" are use synonymously herein.

As used herein, the term "substituted alkyl" refers to an alkyl group, preferably of from 1 to 10 carbon atoms ("substituted lower alkyl"), having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyacylamino, cyano, halogen, hydroxyl, keto, thioketo, carboxyl, carboxylalkyl, thiol, thioalkoxy, substituted thioalkoxy, aryl, aryloxy, heteroaryl, heteroaryloxy, heterocyclic, hydroxyamino, alkoxyamino, nitro, —SO-alkyl, —SO-substituted alkyl, —SO-aryl, —SO, heteroaryl, —S02-alkyl, —SO?-substituted alkyl, —S02-aryl, —S02-heteroaryl, and mono- and di-alkylamino, mono- and di-(substituted alkyl)amino, mono- and di-arylamino, mono- and di-heteroarylamino, mono- and di-heterocyclic amino, and unsymmetric di-substituted amines having different substituents selected from the group consisting of alkyl, aryl, heteroaryl and heterocyclic. As used herein, other moieties having, the prefix "substituted" are intended to include one or more of the substituents listed above.

As used herein, the term "alkoxy" refers to the group "alkyl-O—", where alkyl is as defined above. Preferred alkoxy groups include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

As used herein, the term "alkenyl" refers to alkenyl groups preferably having from 2 to 10 carbon atoms and more preferably 2 to 6 carbon atoms and having at least 1 and preferably from 1–2 sites of alkenyl unsaturation.

Preferred alkenyl groups include ethenyl (—CH=CH2), n-propenyl (—CH2CH=CH2), iso-propenyl (—C(CH3)=CH2), and the like.

As used herein, the term "alkynyl" refers to alkynyl groups preferably having from 2 to 10 carbon atoms and more preferably 2 to 6 carbon atoms and having at least 1 and preferably from 1–2 sites of alkynyl unsaturation.

As used herein, the term "acyl" refers to the groups alkyl-C(O)—, substituted alkyl C(O)—, cycloalkyl-C(O)—, substituted cycloalkyl-C(O)—, aryl-C(O)—, substituted aryl-C(O)—, heteroaryl-C(O)— and heterocyclic-C(O)— where alkyl, substituted alkyl, cycloalkyl, substituted cycloalkyl, aryl, heteroaryl and heterocyclic are as defined herein.

As used herein, the term "acylamino" refers to the group —C(O)NRR where each R is independently hydrogen, alkyl, substituted alkyl, aryl, substituted aryl, heteroaryl, or heterocyclic, wherein alkyl, substituted alkyl, aryl, heteroaryl and heterocyclic are as defined herein.

As used herein, the term "aryl" refers to an unsaturated aromatic carbocyclic group of from 6 to 14 carbon atoms having a single ring, (e.g., phenyl) or multiple condensed (fused) rings (e.g., naphthyl or anthryl).

Preferred aryls include phenyl, naphthyl and the like. Unless otherwise constrained by the definition for the aryl substituent, such aryl groups can optionally be substituted with from 1 to 5 substituents and preferably 1 to 3 substituents selected from the group consisting of acyloxy, hydroxy, acyl, alkyl, alkoxy, alkenyl, alkynyl, substituted alkyl, substituted alkoxy, substituted alkenyl, substituted alkynyl, amino, substituted amino, aminoacyl, acylamino, alkaryl, aryl, aryloxy, azido, carboxyl, carboxylalkyl, cyano, halo, nitro, heteroaryl, heteroaryloxy, heterocyclic, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —S02-alkyl, —S02-substituted alkyl, —S02-aryl, —S02-heteroaryl, trihalomethyl. Preferred substituents include alkyl, alkoxy, halo, cyano, nitro, trihalomethyl, and thioalkoxy.

As used herein, the term "cycloalkyl" refers to cyclic alkyl groups of from 3 to 12 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like.

As used herein, the terms "halo" or "halogen" refer to fluoro, chloro, bromo and iodo and preferably is either fluoro or chloro.

As used herein, the term "heteroaryl" refers to an aromatic carbocyclic group of from 1 to 15 carbon atoms and 1 to 4 heteroatoms selected from the group consisting of oxygen, nitrogen and sulfur within at least one ring (if there is more than one ring).

Unless otherwise constrained by the definition for the heteroaryl substituent, such heteroaryl groups can be optionally substituted with from 1 to 5 substituents and preferably 1 to 3 substituents selected from the group consisting of acyloxy, hydroxy, acyl, alkyl, alkoxy, alkenyl, alkynyl, substituted alkyl, substituted alkoxy, substituted alkenyl, substituted alkynyl, amino, substituted amino, aminoacyl, acylamino, alkaryl, aryl, aryloxy, azido, carboxyl, carboxylalkyl, cyano, halo, nitro, heteroaryl, heteroaryloxy, heterocyclic, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —S02-alkyl, _S02-substituted alkyl, —S02-aryl, —S02-heteroaryl, trihalomethyl. Preferred substituents include alkyl, alkoxy, halo, cyano, nitro, trihalomethyl, and thloalkoxy. Such heteroaryl groups can have a single ring (e.g., pyridyl or furyl) or multiple condensed rings (e.g., indolizinyl or benzothienyl).

"Heterocycle" or "heterocyclic" refers to a monovalent saturated or unsaturated carbocyclic group having a single ring or multiple condensed rings, from 1 to 15 carbon atoms and from 1 to 4 hetero atoms selected from the group consisting of nitrogen, sulfur or oxygen within the ring. Such heterocyclic groups are optionally substituted with 1 to 5 substituents selected from the group consisting of alkyl, substituted alkyl, alkoxy, substituted alkoxy, aryl, aryloxy, halo, nitro, heteroaryl, thiol, thioalkoxy, substituted thioalkoxy, thioaryloxy, trihalomethyl, and the like. Such heterocyclic groups can have a single ring or multiple condensed rings.

As to any of the above groups that contain 1 or more substituents, it is understood, that such groups do not contain any substitution or substitution patterns which are sterically impractical and/or synthetically non-feasible.

"Pharmaceutically acceptable salts" refers to pharmaceutically acceptable salts of a compound of Formulas IA or IB, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like can be used as the pharmaceutically acceptable salt.

The term "protecting group" or "blocking group" refers to any group which when bound to one or more hydroxyl, amino or carboxyl groups of the compounds (including intermediates thereof such as the aminolactams, aminolactones, etc.) prevents reactions from occurring at these groups and which protecting group can be removed by conventional chemical or enzymatic steps to reestablish the hydroxyl, amino or carboxyl group.

Preferred removable amino blocking groups include conventional substituents such as t-butyoxycarbonyl (t-BOC), benzyloxycarbonyl (CBZ), and the like which can be removed by conventional conditions compatible with the nature of the,product.

The compounds of the present invention have the following general formulas IA and IB:

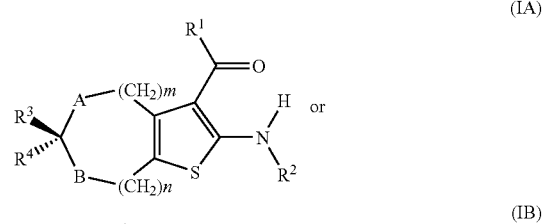

(IA)

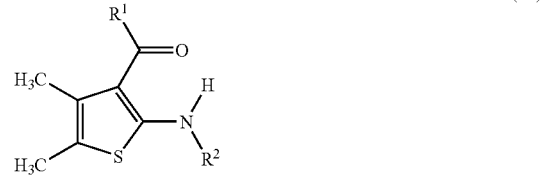

(IB)

wherein:
$R^1$ is

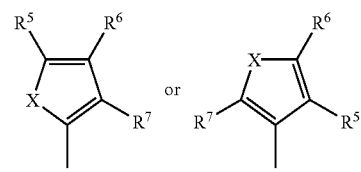

wherein $R^2$ is H, C(=O)$R^8$;
$R^8$ is H, alkyl, substituted alkyl, aralkyl, substituted aralkyl, aryl, or substituted aryl;
$R^3$ and $R^4$ are independently H, alkyl, substituted alkyl, aryl, substituted aryl, aralkyl, alkenyl, substituted alkenyl, alkynyl, substituted alkynyl, halogen, hydroxy, alkylsulfonyloxy, arylsulfonyloxy, substituted arylsulfonyloxy, alkoxy, alkylthio, or arylthio;
or if $R^3$ and $R^4$ are both alkoxy or alkylthio, may form a 1,3-dioxolan-2-yl, 1,3-dioxan-2-yl, 1,3-dithiolan-2-yl, or 1,3-dithian-2-yl group;
or together $R^3$ and $R^4$ may form a-carbonyl oxygen;
$R^5$, $R^6$, and $R^7$ are independently H, alkyl, substituted alkyl, aryl, substituted aryl, halogen, hydroxy, nitro, amino, substituted amino, disubstituted amino, alkoxy, aryloxy, alkylthio, arylthio, sulfonamido, or substituted sulfonamido;
or together $R^5$ and $R^6$ or $R^6$ and $R^7$ may be CH=CH—CH=CH, such that they form a fused aromatic ring;

A and B are independently O, S, or N—R$^8$;

or A and B may independently represent a carbon-carbon single bond;

m and n are independently 0, 1, 2, or 3;

except that A and B cannot both represent a carbon-carbon single bond when m and n are both 0; and X is CH=CH, CH=N, N=CH, O, S, or N—R$^8$.

Those skilled in the art of organic chemistry will appreciate that reactive and fragile functional groups often must be protected prior to a particular reaction, or sequence of reactions, and then restored to their original forms after the last reaction is completed. Usually groups are protected by converting them to a relatively stable derivative. For example, a hydroxyl group may be converted to an ether group and an amino converted to an amide or carbamate. Methods of protecting and de-protect, also know as "blocking" and "de-blocking," are well know and widely practiced in the art, e.g. see T. Green, *Protective Groups in Organic Synthesis*, John Wiley, New York 1981) or *Protective Groups in Organic Chemistry*, Ed. J. F. W. McOmie, Plenum Press, London (1973).

Representative example compounds of the present invention include:

| Example Compound Number | Compound Name |
|---|---|
| 1 | (2-Amino-4,7-dihydro-5H-thieno[2,3-c]thiopyran-3-yl)-phenyl-methanone |
| 2 | (2-Amino-4,7-dihydro-5H-thieno[2,3-c]thiopyran-3-yl)-(4-chlorophenyl)-methanone |
| 3 | (2-Amino-4,5-dihydrothieno[2,3-b]thiophen-3-yl)-(4-chlorophenyl)-methanone |
| 4 | (2-Amino-4,5,6,7-tetrahydrobenzo[b]thiophen-3-yl)-furan-2-yl-methanone |
| 5 | 2-Amino-4,5,6,7-tetrahydrobenzo[b]thiophen-3-yl)-thiophen-2-yl-methanone |
| 6 | (2-Amino-4,5,6,7-tetrahydrobenzo[b]thiophen-3-yl)-naphthalen-1-yl-methanone |
| 7 | (2-Amino-5,6-dihydro-4H-cyclopenta[b]thiophen-3-yl)-naphthalen-1-yl-methanone |
| 8 | (2-Amino-4,5-dimethylthiophen-3-yl)-naphthalen-1-yl-methanone |
| 9 | (2-Amino-6-benzyl-4,5,6,7-tetrahydrothieno[2,3-c]pyridin-3-yl)-naphthalen-1-yl-methanone |
| 10 | N-[3-(Furan-2-carbonyl)-4,5,6,7-tetrahydrobenzo[b]thiophen-2-yl]-acetamide |
| 11 | (2-Amino-5,6-dihydro-4H-cyclopenta[b]thiophen-3-yl)-furan-2-yl-methanone |
| 12 | (2-Amino-6-benzyl-4,5,6,7-tetrahydrothieno[2,3-c]pyridin-3-yl)-furan-2-yl-methanone |
| 13 | (2-Amino-4,5-dimethylthiophen-3-yl)-furan-2-yl-methanone |
| 14 | (2-Amino-4,5,6,7-tetrahydrobenzo[b]thiophen-3-yl)-benzofuran-2-yl-methanone |
| 15 | (2-Amino-5,6-dihydro-4H-cyclopenta[b]thiophen-3-yl)-benzofuran-2-yl-methanone |
| 16 | (2-Amino-6-benzyl-4,5,6,7-tetrahydrothieno[2,3-c]pyridin-3-yl)-benzofuran-2-yl-methanone |
| 17 | 2-Amino-5,6-dihydro-4H-cyclopenta[b]thiophen-3-yl)-pyridin-2-yl-methanone |
| 18 | (2-Amino-4,5-dimethylthiophen-3-yl)-benzofuran-2-yl-methanone |
| 19 | (2-Amino-4,5,6,7-tetrahydrobenzo[b]thiophen-3-yl)-pyridin-2-yl-methanone |
| 20 | (2-Amino-6-benzyl-4,5,6,7-tetrahydrothieno[2,3-c]pyridin-3-yl)-pyridin-2-yl-methanone |
| 21 | (2-Amino-4,5-dimethylthiophen-3-yl)-pyridin-2-yl-methanone |
| 22 | (2-Amino-5,6-dihydro-4H-cyclopenta[b]thiophen-3-yl)-(4-bromonaphthalen-1-yl)-methanone |
| 23 | (2-Amino-5,6-dihydro-4H-cyclopenta[b]thiophen-3-yl-(4-methoxynaphthalen-1-yl)-methanone |
| 24 | (2-Amino-5,6-dihydro-4H-cyclopenta[b]thiophen-3-yl-(4-iodonaphthalen-1-yl)-methanone |
| 25 | (2-Amino-5,6-dihydro-4H-cyclopenta[b]thiophen-3-yl-(4-chloronaph-thalen-1-yl)-methanone |
| 26 | (2-Amino-4,5,6,7-tetrahydrobenzo[b]thiophen-3-yl)-(4-iodonaphthalen-1-yl)-methanone |
| 27 | (2-Amino-4,5,6,7-tetrahydrobenzo[b]thiophen-3-yl)-(4-methoxynaph-thalen-1-yl)-methanone |
| 28 | (2-Amino-4,5,6,7-tetrahydrobenzo[b]thiophen-3-yl)-(4-chloronaphthalen-1-yl)-methanone |
| 29 | (2-Amino-4,5,6,7-tetrahydrobenzo[b]thiophen-3-yl)-(4-bromonaphthalen-1-yl)-methanone |
| 30 | (2-Amino-4,5,6,7-tetrahydrobenzo[b]thiophen-3-yl)-naphthalene-2-yl-methanone |
| 31 | (2-Amino-5,6-dihydro-4H-cyclopenta[b]thiophen-3-yl)-naphthalen-2-yl-methanone |

-continued

| Example Compound Number | Compound Name |
|---|---|
| 32 | (2-Amino-6-benzyl-4,5,6,7-tetrahydrothieno[2,3-c]pyridin-3-yl)-naphthalen-2-yl-methanone |
| 33 | (2-Amino-4,5-dimethylthiophen-3-yl)-naphthalen-2-yl-methanone |
| 34 | (2-Amino-6-spiro(1,4-dioxolan-2-yl)-4,5,6,7-tetrahydrobenzo[b]thiophen-3-yl)-(4-chlorophenyl)-methanone |
| 35 | (2-Amino-5,6-dihydro-4H-cyclopenta[b]thiophen-3-yl)-thiophen-2-yl-methanone |
| 36 | (2-Amino-4,5-dimethylthiophen-3-yl)-thiophen-2-yl-methanone |
| 37 | (2-Amino-6-hydroxy-4,5,6,7-tetrahydrobenzo[b]thiophen-3-yl)-(4-chlorophenyl)-methanone |
| 38 | (2-Amino-6-benzyl-4,5,6,7-tetrahydrothieno[2,3-c]pyridin-3-yl)-thiophen-2-yl-methanone |
| 39 | (2-Amino-4,5,6,7-tetrahydrobenzo[b]thiophen-3-yl)-(5-bromothiophen-2-yl)-methanone |
| 40 | (2-Amino-5,6-dihydro-4H-cyclopenta[b]thiophen-3-yl)-(5-bromothio-phen-2-yl)-methanone |
| 41 | (2-Amino-4,5-dimethylthiophen-3-yl)-(5-bromothiophen-2-yl)-methanone |
| 42 | (2-Amino-6-benzyl-4,5,6,7-tetrahydrothieno[2,3-c]pyridin-3-yl)-(5-bromothiophen-2-yl)-methanone |
| 43 | (2-Amino-4,5,6,7-tetrahydrobenzo[b]thiophen-3-yl)-(5-chlorothiophen-2-yl)-methanone |
| 44 | (2-Amino-5,6-dihydrocyclopenta[b]thiophen-3-yl)-(5-chlorothiophen-2-yl)-methanone |
| 45 | (2-Amino-4,5-dimethylthiophen-3-yl)-(5-chlorothiophen-2-yl)-methanone |
| 46 | (2-Amino-6-benzyl-4,5,6,7-tetrahydrothieno[2-3-c]pyridin-3-yl)-(5-chlorothiophen-2-yl)-methanone |
| 47 | (2-Amino-4,5,6,7-tetrahydrobenzo[b]thiophen-3-yl)-thiophen-3-yl-methanone |
| 48 | (2-Amino-5,6-dihydro-4H-cyclopenta[b]thiophen-3-yl)-thiophen-3-yl-methanone |
| 49 | (2-Amino-4,5-dimethylthiophen-3-yl)-thiophen-3-yl-methanone |
| 50 | (2-Amino-6-benzyl-4,5,6,7-tetrahydrothieno[2,3-c]pyridin-3-yl)-thiophen-3-yl-methanone |
| 51 | [2-Amino-6-(4-methoxyphenyl)-4H-1,5,7-trithia-inden-3-yl]-napthalen-1-yl-methanone |
| 52 | [2-Amino-6-(4-methoxyphenyl)-4H-1,5,7-trithia-inden-3-yl]-(4-chlorophenyl)-methanone |
| 53 | [2-Amino-6-(4-methoxyphenyl)-4H-1,5,7-trithia-inden-3-yl]-thiophen-2-yl-methanone |
| 54 | (2-Amino-4,5,6,7-tetrahydrobenzo[b]thiophen-3-yl)-(9H-fluoren-2-yl)-methanone |
| 55 | (2-Amino-5,6-dihydro-4H-cyclopenta[b]thiophen-3-yl)-(9H-fluoren-2-yl)-methanone |
| 56 | (2-Amino-6-benzyl-4,5,6,7-tetrahydrothieno[2,3-c]pyridin-3-yl)-(9H-fluor-en-2-yl)-methanone |
| 57 | [2-Amino-6-[(methanesulfonyl)oxy]-4,5,6,7-tetrahydrobenzo[b]thiophen-3-yl]-(4-chlorophenyl)-methanone |
| 58 | [2-Amino-6-(4-chlorobenzyl)-4,5,6,7-tetrahydrothieno[2,3-c]pyridin-3-yl]-naphthalen-2-yl-methanone |
| 59 | 2-Amino-6-(4-fluorobenzyl)-4,5,6,7-tetrahydrothieno[2,3-c]pyridin-3-yl]-naphthalen-2-yl-methanone |
| 60 | (2-Amino-6-benzyl-4,5,6,7-tetrahydrobenzo[b]thiophen-3-yl)-naphthalen-2-yl-methanone |
| 61 | [2-Amino-6-(2-fluorobenzyl)-4,5,6,7-tetrahydrothieno[2,3-c]pyridin-3-yl]-naphthalen-2-yl-methanone |
| 62 | [2-Amino-6-(2-chlorobenzyl)-4,5,6,7-tetrahydrothieno[2,3-c]pyridin-3-yl]-naphthalen-2-yl-methanone |
| 63 | [2-Amino-6-(3,4,5-trimethoxybenzyl)-4,5,6,7-tetrahydrothieno[2,3-c]pyri-din-3-yl]-naphthalen-2-yl-methanone |
| 64 | (2-Amino-6-benzyl-4,5,6,7-tetrahydrobenzo[b]thiophen-3-yl)-thiophen-2-yl-methanone |
| 65 | (2-Amino-6-benzyl-4,5,6,7-tetrahydrobenzo[b]thiophen-3-yl)-thiophen-3-yl-methanone |
| 66 | (2-Amino-6-benzyl-4,5,6,7-tetrahydrobenzo[b]thiophen-3-yl)-(4-chlorophenyl)-methanone |
| 67 | (2-Amino-6-benzyl-4,5,6,7-tetrahydrobenzo[b]thiophen-3-yl)-naphthalen-2-yl-methanone |
| 68 | [2-Amino-6-(4-nitrobenzyl)-4,5,6,7-tetrahydrobenzo[b]thiophen-3-yl]-naphthalen-2-yl-methanone |

Synthesis of Compounds

Compounds of formula IA may be conveniently prepared according to Scheme 1. A compound of formula (II) or (III) is reacted with a compound of formula (IV) in the presence of elemental sulfur and morpholine at approximately 70° C., for about one hour, then at approximately 20 to 25° C. for a period of about 20 hours to yield a compound of formula (IA).

SCHEME 1

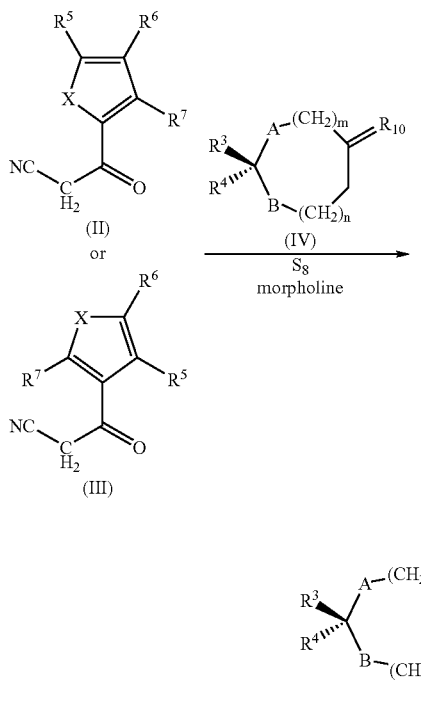

Compounds of formula (IB) may be conveniently prepared according to Scheme 2. In a manner analogous to that used for preparing compounds of formula (IA), 2-butanone is reacted with a compound of formula (II) or (III) in the presence of elemental sulfur and morpholine at approximately 70° C., for about one hour, then at approximately 20 to 25° C., for a period of about 20 hours, to afford a compound of formula (IB).

SCHEME 2

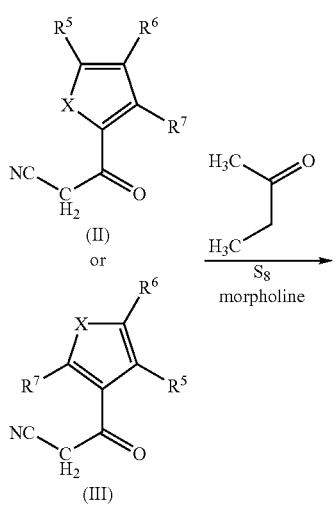

-continued

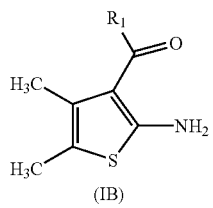

Compounds of formula (II) or (III) may be conveniently prepared according to Scheme 3 by treating compounds of formula (V) or (VI) with bromine in glacial acetic acid at approximately 20 to 25° C. for approximately two hours to provide intermediates of formula (VII) or (VIII). These intermediates in a protic solvent, such as ethanol, may then be treated with an aqueous solution of potassium cyanide at approximately 20 to 25° C. for about 20 to 24 hours to afford compounds of formula (II) or (III).

SCHEME 3

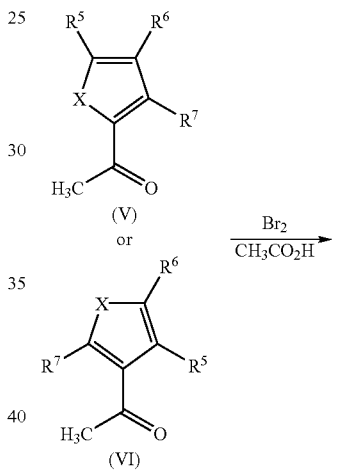

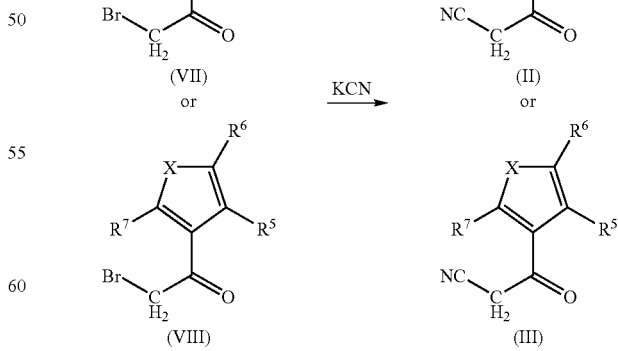

Compounds of formula (IV), (V), or (VI) are commercially available or may be prepared by methods known in the literature.

Utility

The compounds can be used for:

Protection against hypoxia and/or ischemia induced injuries (e.g., stroke, infarction);

Treatment of adenosine-sensitive cardiac arrhythmias;

antinociception (i.e., analgesics);

anticonvulsants;

cardioprotection, short term (e.g., prior to percutaneous angioplasty (PTDA), angioplasty, and cardiac surgeries) and long term (prevention of myocardial infarction, especially in high risk patients, reduction of infarct damage, especially in high risk patients);

treatment of congestive heart failure;

neuroprotection: stroke prevention, stroke treatment, treatment of Alzheimer's disease and treatment of epilepsy;

pain management generally, including different forms of neuropathic pain, e.g., diabetic neuropathy, post herpetic neuralgia;

antilipid uses: reduction of free fatty acids, triglycerides, glucose;

adjunct therapy in diabetes, including, insulin dependent and non-insulin dependent diabetes mellitus: stimulation of insulin secretion from the pancreas, increase in tissue sensitivity to insulin;

treatment of GI disorders such as diarrhea, irritable bowel disease, irritable bowel syndrome, irritable bladder, incontinence such as urge incontinence;

treatment of glaucoma;

treatment of sleep diorders, such as sleep apnea;

treatment of cardiac disarrythmias (peroxysmal supraventricular tachycardia;

use in combination with anesthesia for post surgical pain;

treatment of inflammation;

diagnostic uses, for example, to determine the presence of one or more of the above described medical conditions, or in a screening assay to determine the effectiveness of other compounds for bindinor to the AI Ado receptor (i.e., through competitive inhibition as determined by various binding assays); and Other indications for which $A_1$AdoR agonists are used.

The amount of compound of the present invention required to be effective as an allosteric modulator of an adenosine receptor will, of course, vary with the individual mammal being treated and is ultimately at the discretion of the medical or veterinary practitioner. The factors to be considered include the condition being treated, the route of administration, the nature of the formulation, the mammal's body weight, surface area, age and general condition, and the particular compound to be administered. However, a suitable effective dose is in the range of about 0.1 μg/kg to about 10 mg/kg body weight per day, preferably in the range of about 1 mg/kg to about 3 mg/kg per day.

The total daily dose may be given as a single dose, multiple doses, e.g., two to six times per day, or by intravenous infusion for a selected duration. Dosages above or below the range cited above are within the scope of the present invention and may be administered to the individual patient if desired and necessary. For example, for a 75 kg mammal, a dose range would be about 75 mg to about 220 mg per day, and a typical dose would be about 150 mg per day. If discrete multiple doses are indicated, treatment might typically be 50 mg of a compound of the present invention given 3 times per day.

Biological Assays.

Chinese hamster ovary cells expressing human recombinant $A_1$ adenosine receptors (CHO:huA1 cells) at a density of approximately 8000 fmol/mg protein were prepared as previously described (Kollias-Baker et al., (1997), *J. Pharmacol. Exp. Ther.* 281: 761–768) and aliquots of the cells at low passage numbers were frozen and stored in liquid nitrogen. When compounds were tested, an aliquot of CHO:huA1 cells were rapidly thawed after removal from liquid nitrogen, then grown in Ham's F12 culture medium with 10% fetal bovine serum and 0.5 mg/mL of antibiotic G-418 (Shryock, Ozeck, and Belardinelli (1998), *Mol. Pharmacol* 53: 886–893). Cells were passaged thrice weekly. Aliquots of cells were placed into 12-well plates with culture medium, serum, and antibiotic for 48 hours, by which time the cells had grown to a confluent monolayer.

Allosteric enhancement was measured as the action of a test compound at different concentrations (0.01, 0.1, 1 and 10 μM) to reduce the cAMP content of CHO:huA1 cells. To initiate an experiment, growth medium was removed from the 12-well plates and cells were washed once with warm Hanks' buffered saline. The wash solution was then removed and replaced with fresh Hanks' solution containing forskolin (1 μM), rolipram (20 μM), $N^6$-cyclopentyladenosine (CPA, 0.01 nM), adenosine deaminase (2 U/mL), and the test compound. Forskolin was used to stimulate the activity of adenylyl cyclase, rolipram to inhibit cAMP phosphodiesterase, adenosine deaminase to degrade endogenous adenosine, and CPA to cause a small increase of the number of activated adenosine receptors. After 6 min of incubation at 36° C. in the presence of test compound, the incubation solution was removed and hydrochloric acid (final concentration 50 mM) was added to terminate drug action.

The content of cAMP in acidified extracts of cells was determined by radioimmunoassay as previously described (Kollias-Baker et al., (1997), *J. Pharmacol. Exp. Ther.* 281: 761–768). Because the magnitude of the effects of allosteric enhancers on CHO:huA1 cells changed subtly with passage number and differed slightly among different aliquots of cells, the actions of the test compounds and the action of a reference compound (PD 81,723) were assessed in each experiment. The effect of each test compound on cAMP content is presented in Table 1 as a percentage of the value of cAMP content in the absence of drug (control, 100%). Each value is a mean±standard error of 6 determinations in each of the number of experiments indicated in the "n" column of the table.

TABLE 1

Percentage Change in CHO Cell cAMP Content in Presence of 2-Amino-3-Acyl-Thiophenes

| Example Compound Number | n | Change in cAMP Content from Control (mean + SEM) Concentration of Test Compound | | | |
|---|---|---|---|---|---|
| | | 0.01 μM | 0.1 μM | 1 μM | 10 μM |
| 1 | 3 | 9 ± 4 | −6 ± 3 | −15 ± 2 | −35 ± 2 |
| 2 | 3 | 15 ± 3 | −10 ± 4 | 16 ± 5 | −0.3 ± 5 |
| 3 | 3 | −1 ± 4 | 11 ± 4 | 1 ± 3 | −35 ± 4 |
| 4 | 3 | −10 ± 2 | 2 ± 6 | −3 ± 6 | −10 ± 7 |
| 5 | 3 | −11 ± 3 | −11 ± 5 | −16 ± 3 | −40 ± 2 |
| 6 | 3 | −11 ± 4 | −15 ± 4 | −22 ± 3 | −52 ± 3 |
| 7 | 3 | −0.6 ± 3 | −6 ± 1 | −29 ± 4 | −60 ± 1 |
| 8 | 3 | −0.6 ± 2 | −3 ± 3 | 6 ± 5 | −45 ± 2 |
| 9 | 3 | −21 ± 3 | −7 ± 4 | −25 ± 4 | 19 ± 2 |
| 10 | 3 | −8 ± 5 | −14 ± 4 | −25 ± 5 | 8 ± 5 |
| 11 | 3 | 3 ± 4 | −14 ± 4 | −0.8 ± 3 | −23 ± 2 |

TABLE 1-continued

Percentage Change in CHO Cell cAMP Content in Presence of 2-Amino-3-Acyl-Thiophenes

| Example Compound Number | n | Change in cAMP Content from Control (mean + SEM) Concentration of Test Compound | | | |
|---|---|---|---|---|---|
| | | 0.01 µM | 0.1 µM | 1 µM | 10 µM |
| 12 | 3 | −27 ± 4 | −0.6 ± 4 | −15 ± 3 | −8 ± 11 |
| 13 | 3 | −4 ± 5 | 11 ± 5 | −7 ± 5 | 5 ± 10 |
| 14 | 3 | −13 ± 5 | −3 ± 4 | −4 ± 3 | −5 ± 4 |
| 15 | 3 | −5 ± 3 | −13 ± 3 | 3 ± 5 | −4 ± 6 |
| 16 | 3 | 4 ± 3 | 14 ± 4 | −10 ± 2 | 11 ± 4 |
| 17 | 3 | −3 ± 4 | 0.8 ± 7 | −1 ± 6 | 2 ± 7 |
| 18 | 3 | 6 ± 5 | −7 ± 4 | 16 ± 5 | 7 ± 6 |
| 19 | 3 | −2 ± 4 | −8 ± 5 | −11 ± 5 | 8 ± 3 |
| 20 | 3 | 2 ± 4 | 7 ± 5 | 0.1 ± 5 | 31 ± 3 |
| 21 | 3 | 0.7 ± 3 | −8 ± 3 | 4 ± 4 | 14 ± 4 |
| 22 | 3 | 3 ± 3 | 19 ± 5 | −14 ± 5 | −67 ± 3 |
| 23 | 3 | −6 ± 3 | −3 ± 4 | −8 ± 4 | −35 ± 3 |
| 24 | 3 | −6 ± 3 | −8 ± 3 | −22 ± 4 | −75 ± 1 |
| 25 | 3 | −10 ± 2 | −15 ± 4 | −27 ± 2 | −55 ± 2 |
| 26 | 3 | −3 ± 4 | −4 ± 4 | −24 ± 5 | −67 ± 2 |
| 27 | 3 | 5 ± 4 | −5 ± 4 | −3 ± 3 | −17 ± 1 |
| 28 | 3 | −11 ± 3 | 3 ± 3 | −25 ± 4 | −44 ± 2 |
| 29 | 3 | −6 ± 3 | −10 ± 2 | −29 ± 2 | −72 ± 1 |
| 30 | 3 | −13 ± 4 | −24 ± 3 | −28 ± 2 | −42 ± 3 |
| 31 | 3 | −19 ± 3 | −14 ± 4 | −15 ± 3 | −51 ± 3 |
| 32 | 3 | −11 ± 4 | −12 ± 3 | −18 ± 3 | −60 ± 4 |
| 33 | 3 | −1 ± 3 | −4 ± 3 | −8 ± 3 | −28 ± 3 |
| PD81,723 | 33 | −1 ± 2 | −7 ± 2 | −13 ± 1 | −50 ± 1 |

Radioligand Binding Assays Results

Methods for detecting specific macromolecular species, such as proteins, drugs, and polynucleotides, have proven to be very valuable analytical techniques in biology and medicine, particularly for characterizing the molecular composition of normal and abnormal tissue samples and genetic material. Many different types of such detection methods are widely used in biomedical research and clinical laboratory medicine. Examples of such detection methods include: immunoassays, immunochemical staining for microscopy, fluorescence-activated cell sorting (FACS), nucleic acid hybridization, water sampling, air sampling, and others. Typically, a detection method employs at least one analytical reagent that binds to a specific target macromolecular species and produces a detectable signal. These analytical reagents typically have two components: (1) a probe macromolecule, for example, an antibody or oligonucleotide, that can bind a target macromolecule with a high degree of specificity and affinity, and (2) a detectable label, such as a radioisotope or covalently-linked fluorescent dye molecule. In general, the binding properties of the probe macromolecule define the specificity of the detection method, and the detectability of the associated label determines the sensitivity of the detection method. The sensitivity of detection is in turn related to both the type of label employed and the quality and type of equipment available to detect it.

For example, radioimmunoassays (RIA) have been among the most sensitive and specific analytical methods used for detecting and quantitating biological macromolecules. Radioimmunoassay techniques have been used to detect and measure minute quantities of specific analytes, such as polypeptides, drugs, steroid hormones, polynucleotides, metabolites, and tumor markers, in biological samples. Radioimmunoassay methods employ immunoglobulins labeled with one or more radioisotopes as the analytical reagent. Radiation (alpha, beta, or gamma) produced by decay of the attached radioisotope label serves as the signal that can be detected and quantitated by various radiometric methods.

The term "labeled analog" is further understood to encompass compounds which are labeled with radioactive isotopes, such as but not limited to tritium ($^3$H), carbon ($^{14}$C), iodine ($^{125}$I), phosphorus ($^{31}$P, $^{32}$P, $^{33}$P), sulfur ($^{35}$S) or otherwise labeled (e.g. fluorescently). Less common, but also known in the art, is the use of radio labels of the positron emitting radionuclides $^{11}$C, $^{13}$N, $^{15}$O, $^{18}$F or $^{76}$Br. Also known in the art, but less common, is the use of stable isotopes, such as deuterium ($^2$H) and $^{13}$C that are detected by magnetic resonance imaging or mass spectrometry. The compounds of this invention may be labeled or derivatized, for example, for kinetic binding experiments, for further elucidating metabolic pathways and enzymatic mechanisms, or for characterization by methods known in the art of analytical chemistry.

Formulations

Formulations of the present invention for medical use comprise an active compound, i.e., a compound of formula (IA), (IB) or (IC), together with an acceptable carrier thereof and optionally other therapeutically active ingredients. The carrier must be pharmaceutically acceptable in the sense of being compatible with the other ingredients of the formulation and not deleterious to the recipient thereof.

The present invention, therefore, further provides a pharmaceutical formulation comprising a compound of formula (IA), (IB) or (IC) together with a pharmaceutically acceptable carrier thereof.

The formulations include, but are not limited to, those suitable for oral, rectal, topical or parenteral (including subcutaneous, intramuscular and intravenous) administration. Preferred are those suitable for oral or parenteral administration.

The formulations may conveniently be presented in unit dosage form and may be prepared by any of the methods well known in the art of pharmacy. All methods include the step of bringing the active compound into association with a carrier that constitutes one or more accessory ingredients. In general, the formulations are prepared by uniformly and intimately bringing the active compound into association with a liquid carrier or a finely divided solid carrier and then, if necessary, shaping the product into desired unit dosage form.

Formulations of the present invention suitable for oral administration may be presented as discrete units such as capsules, cachets, tablets or lozenges, each containing a predetermined amount of the active compound; as a powder or granules; or a suspension or solution in an aqueous liquid or non-aqueous liquid, e.g., a syrup, an elixir, an emulsion or a draught.

A tablet may be made by compression or molding, optionally with one or more accessory ingredients. Compressed tablets may be prepared by compressing in a suitable machine the active compound in a free-flowing form, e.g., a powder or granules, optionally mixed with accessory ingredients, e.g., binders, lubricants, inert diluents, surface active or dispersing agents. Molded tablets may be made by molding in a suitable machine, a mixture of the powdered active compound with any suitable carrier.

A syrup or suspension may be made by adding the active compound to a concentrated, aqueous solution of a sugar, e.g., sucrose, to which may also be added any accessory ingredients. Such accessory ingredients) may include flavoring, an agent to retard crystallization of the sugar or an agent to increase the solubility of any other ingredient, e.g., as a polyhydric alcohol, for example, glycerol or sorbitol.

Formulations for rectal administration may be presented as a suppository with a conventional carrier, e.g., cocoa butter or Witepsol S55 (trademark of Dynamite Nobel Chemical, Germany), for a suppository base.

Formulations suitable for parenteral administration conveniently comprise sterile aqueous preparation of the active compound that is preferably isotonic with the blood of the recipient. Thus, such formulations may conveniently contain distilled water, 5% dextrose in distilled water or saline. Useful formulations also comprise concentrated solutions or solids containing the compound of formula (I) that upon dilution with an appropriate solvent give a solution suitable for parental administration above.

Topical formulations include ointments, creams, gels and lotions that may be prepared by conventional methods known in the art of pharmacy. In addition to the ointment, cream gel, or lotion base and the active ingredient, such topical formulation may also contain preservatives, perfumes, and additional active pharmaceutical agents.

In addition to the aforementioned ingredients, the formulations of this invention may further include one or more optional accessory ingredient(s) utilized in the art of pharmaceutical formulations, e.g., diluents, buffers, flavoring agents, binders, surface active agents, thickeners, lubricants, suspending agents, preservatives (including antioxidants) and the like.

EXAMPLES

The following examples illustrate aspects of this invention but should not be construed as limitations. The symbols and conventions used in these examples are indented to be consistent with those used in the contemporary, international, chemical literature, for example, the *Journal of the American Chemical Society and Tetrahedron.*

Example 1

(2-Amino-4,7-dihydro-5
H-thieno[2,3-c]thiopyran-3-yl)-phenyl-methanone

Step A. 2-Bromoacetophenone: To a solution of acetophenone (10 mmol, Aldrich) in 10 ml of glacial acetic acid, was added bromine (10 mmol, 0.51 mL) dropwise and the mixture was stirred at room temperature for 2 h. After this time, the acetic acid was evaporated under reduced pressure at a temperature lower than 40° C. The crude product so obtained was used for the next reaction without purification.

Step B. Benzoylacetonitrile: The crude 2-bromoacetophenone, previously prepared in Step A, was dissolved in 95% EtOH (15 ml). A solution of potassium cyanide (3.6 g, 55 mmol), dissolved in water (5 ml), was added in one portion and the mixture was stirred at room temperature for 24 h. The mixture was then poured onto a mixture of crushed ice and water and acidified with glacial acetic acid (pH=5–6). The resulting solid was collected by filtration and washed with water.

Step C. (2-Amino-4,7-dihydro-5H-thieno[2,3-c]thiopyran-3-yl)-phenyl-methanone: A mixture of benzoylacetonitrile (5 mmol, prepared in Step B), tetrahydro-4 H-thiopyran-4-one (5 mmol, Aldrich), morpholine (0.44 mL, 5 mmol), and sulfur (164 mg, 5 mmol) was heated at 70° C. for 1 h, then stirred at room temperature for 20 h. At the end of this period, the solvent was evaporated under reduced pressure and the residue diluted with ethyl acetate. After washing with water, the organic layer was dried over $Na_2SO_4$, filtered, and evaporated. The crude product was purified by flash column chromatography, then recrystallized from petroleum ether. Yield: 68%; $^1$H NMR ($CDCl_3$): δ 2.18 (t, 2H, J=5.6 Hz), 2.58 (t, 2H, J=5.6 Hz), 3.63 (s, 2H), 6.57 (bs, 2H), 7.51 (m, 5H); yellow solid, mp: 92–95° C. (petroleum ether).

In an analogous manner, the following compounds are prepared by the procedures of Scheme 1 taught above in Example 1, using appropriate precursor compounds, as indicated. If the appropriate precursors are not available, they are prepared as indicated in the following examples:

Example 2

(2-Amino-4,7-dihydro-5
H-thieno[2,3-c]thiopyran-3-yl)-(4-chlorophenyl)-methanone The procedure of Example 1 was followed except that 4-chloroacetophenone (Aldrich) was used in place of acetophenone to prepare the corresponding 2-(4-chlorobenzoyl)acetonitrile (Steps A and B). Tetrahydro-4 H-thiopyran-4-one (Aldrich), 2-(4-chlorobenzoyl)acetonitrile, morpholine, and sulfur were reacted according to the procedure of Step C, Example 1, to afford the desired compound. Yield: 66%; $^1$H NMR ($CDCl_3$): δ 2.18 (t, 2H, J=5.6 Hz), 2.60 (t, 2H, J=5.6 Hz), 3.63 (s, 2H), 6.62 (bs, 2H), 7.39 (d, J=7.6 Hz, 2H), 7.47 (d, J=7.6 Hz, 2H); yellow solid, mp: 142–146° C. (petroleum ether).

Example 3

(2-Amino-4,5-dihydrothieno[2,3-b]thiophen-3-yl)-(4-chlorophenyl)-methanone

The procedure of Example 1 was followed except that 4-chloroacetophenone (Aldrich) was used in place of acetophenone to prepare the corresponding 2-(4-chlorobenzoyl)acetonitrile (Steps A and B). Tetrahydrothiophen-3-one (Aldrich), 2-(4-chlorobenzoyl)acetonitrile, morpholine, and sulfur were reacted according to the procedure of Step C, Example 1, to afford the desired compound. Yield: 59%; $^1$H NMR ($CDCl_3$): δ 2.38 (t, 2H, J=7.8 Hz), 3.51 (t, 2H, J=7.8 Hz), 6.89 (bs, 2H), 7.42 (m, 4H); orange solid, mp: 146–150° C. (petroleum ether).

Example 4

(2-Amino-4,5,6,7-tetrahydrobenzo[b]thiophen-3-yl)-furan-2-yl-methanone

The procedure of Example 1 was followed except that 2-acetylfuran (Aldrich) was used in place of acetophenone to prepare the corresponding 2-(2-furanoyl)acetonitrile (Steps A and B). Cyclohexanone (Aldrich), 2-(2-furanoyl)acetonitrile, morpholine, and sulfur were reacted according to the procedure of Step C, Example 1, to afford the desired compound. Yield: 40%; $^1$H NMR ($CDCl_3$): δ 1.63 (m, 2H), 1.82 (m, 2H), 2.28 (t, 2H, J=5.8 Hz), 2.57 (t, 2H, J=5.8 Hz), 6.20 (bs, 2H), 6.53 (m, 1H), 6.99 (d, 1H, J=3.4 Hz), 7.55 (d, 1H, J=3.4 Hz); yellow solid, mp: 121–122° C. (petroleum ether).

Example 5

2-Amino-4,5,6,7-tetrahydrobenzo[b]thiophen-3-yl)-thiophen-2-yl-methanone

The procedure of Example 1 was followed except that 2-acetylthiophene (Aldrich) was used in place of acetophenone to prepare the corresponding 2-(thiophene-2-carbonyl)acetonitrile (Steps A and B). Cyclohexanone (Aldrich), 2-(thiophene-2-carbonyl)acetonitrile, morpholine, and sulfur were reacted according to the procedure of Step C, Example 1, to afford the desired compound. Yield: 56%; $^1$H NMR (CDCl$_3$): δ 1.59 (m, 2H), 1.81 (m, 2H), 2.20 (m, 2H), 2.54 (m, 2H), 6.10 (bs, 2H), 7.06 (dd, 1H, J=4.8 and 3.6 Hz), 7.38 (d, 1H, J=3.6 Hz), 7.60 (d, 1H, J=4.2 Hz); orange solid, mp: 115–118° C. (petroleum ether).

Example 6

(2-Amino-4,5,6,7-tetrahydrobenzo[b]thiophen-3-yl)-naphthalen-1-yl-methanone

The procedure of Example 1 was followed except that 1'-acetonaphthone (Aldrich) was used in place of acetophenone to prepare the corresponding 2-(naphthalen-1-carbonyl)acetonitrile (Steps A and B). Cyclohexanone (Aldrich), 2-(naphthalen-1-carbonyl)acetonitrile, morpholine, and sulfur were reacted according to the procedure of Step C, Example 1, to afford the desired compound. Yield: 73%; IR (KBr) cm$^{-1}$: 3335, 3235, 3124, 1559, 1430, 1290, 781; $^1$H NMR (CDCl$_3$): δ 1.29 (m, 4H), 1.50 (t, 2H, J=6.0 Hz), 2.44 (t, 2H, J=6.2 Hz), 7.47 (m, 4H), 7.85 (m, 4H), 8.28 (d, 1H, J=6.4 Hz); orange solid, mp: 137–140° C. (ethanol).

Example 7

(2-Amino-5,6-dihydro-4H-cyclopenta[b]thiophen-3-yl)-naphthalen-1-yl-methanone

The procedure of Example 1 was followed except that 1'-acetonaphthone (Aldrich) was used in place of acetophenone to prepare the corresponding 2-(naphthalen-1-carbonyl)acetonitrile (Steps A and B). Cyclopentanone (Aldrich), 2-(naphthalen-1-carbonyl)acetonitrile, morpholine, and sulfur were reacted according to the procedure of Step C, Example 1, to afford the desired compound. Yield: 89%; IR (KBr) cm$^{-1}$: 3328, 3102, 2853, 1582, 1444, 1290, 1255, 1032,780; $^1$H NMR (CDCl$_3$): δ 1.28 (m, 2H), 1.87 (t, 2H, J=7.0 Hz), 2.54 (t, 2H, J=7.2 Hz), 7.41 (d, 1H, J=6.4 Hz), 7.59 (m, 3H), 7.73 (d, 1H, J=8.8 Hz), 8.02 (d, 2H, J=8.6 Hz), 8.73 (bs, 2H); yellow solid, mp: 255–257° C. (petroleum ether).

Example 8

(2-Amino-4,5-dimethylthiophen-3-yl)-naphthalen-1-yl-methanone

The procedure of Example 1 was followed except that 1'-acetonaphthone (Aldrich) was used in place of acetophenone to prepare the corresponding 2-(naphthalen-1-carbonyl)acetonitrile (Steps A and B). 2-Butanone (Aldrich), 2-(naphthalen-1-carbonyl)acetonitrile, morpholine, and sulfur were reacted according to the procedure of Step C, Example 1, to afford the desired compound. Yield: 38%; IR (KBr) cm$^{-1}$: 3358, 3242, 1576, 1426, 1282, 1253, 781; $^1$H NMR (CDCl$_3$): δ 1.16 (s, 3H), 2.07 (s, 3H), 7.17 (bs, 2H), 7.49 (m, 4H), 7.89 (m, 3H); yellow solid, mp: 195–197° C. (petroleum ether).

Example 9

(2-Amino-6-benzyl-4,5,6,7-tetrahydrothieno[2,3-c]pyridin-3-yl)-naphthalen-1-yl-methanone The procedure of Example 1 was followed except that 1'-acetonaphthone (Aldrich) was used in place of acetophenone to prepare the corresponding 2-(naphthalen-1-carbonyl)acetonitrile (Steps A and B). 1-Benzyl-4-piperidone (prepared according to the procedure of van der Klein et al., (1999) *J. Med. Chem.* 42: 3629–3635), 2-(naphthalen-1-carbonyl)acetonitrile, morpholine, and sulfur were reacted according to the procedure of Step C, Example 1, to afford the desired compound. Yield: 65%; IR (KBr) cm$^{-1}$: 3435, 1576, 1426, 1358, 1253, 784; $^1$H NMR (CDCl$_3$): δ 1.53 (m, 2H), 2.30 (m, 2H), 3.38 (s, 2H), 3.54 (s, 2H), 7.43 (m, 11H), 7.88 (m, 3H); yellow solid, mp: 178–180° C. (petroleum ether).

Example 10

N-[3-(Furan-2-carbonyl)-4,5,6,7-tetrahydrobenzo[b]thiophen-2-yl]-acetamide

To a stirred solution of (2-Amino-4,5,6,7-tetrahydrobenzo[b]thiophen-3-yl)-furan-2-yl-methanone (Example 4, 200 mg, 0.8 mmol) in dichloromethane (5 mL), cooled to 4° C. with an ice-water bath, was added triethylamine (0.12 mL, 0.88 mmol), followed by acetyl chloride (0.062 mL, 0.88 mmol). The mixture was warmed to room temperature, stirred for 12 hours, diluted with dichloromethane (5 mL), and washed with 5% aqueous HCl (5 mL), followed by saturated aqueous NaHCO3 (5 mL). The organic phase was dried (Na2SO4), filtered, and evaporated, and the residue precipitated with ethyl acetate and petroleum ether. Yield: 69%; IR (KBr) cm$^{-1}$: 3448, 3118, 2931, 1677, 1606, 1529, 1466, 1432, 1267, 1063, 774; $^1$H NMR (CDCl$_3$): δ 1.67 (m, 2H), 1.86 (m, 2H), 2.26 (s, 3H), 2.38 (t, 2H, J=6.0 Hz), 2.72 (t, 2H, J=7.4 Hz), 6.58 (m, 1H), 7.12 (d, 1H, J=3.4 Hz), 7.63 (s, 1H), 10.7 (s, 1H); yellow solid, mp: 126–127° C. (petroleum ether).

Example 11

(2-Amino-5,6-dihydro-4H-cyclopenta[b]thiophen-3-yl)-furan-2-yl-methanone

The procedure of Example 1 was followed except that 2-acetylfuran (Aldrich) was used in place of acetophenone to prepare the corresponding 2-(2-furanoyl)acetonitrile (Steps A and B). Cyclopentanone (Aldrich), 2-(2-furanoyl)acetonitrile, morpholine, and sulfur were reacted according to the procedure of Step C, Example 1, to afford the desired compound. Yield: 59%; IR (KBr) cm$^{-1}$: 3115, 1560, 1476, 1429, 1288, 1021, 746; $^1$H NMR (CDCl$_3$): δ 2.3 (m, 2H), 2.73 (t, 4H, J=6 Hz), 6.53 (m, 1H), 6.81 (bs, 2H), 7.05 (d, 1H, J=3.4 Hz), 7.55 (s, 1H); yellow solid, mp: 149–153° C. (petroleum ether).

Example 12

(2-Amino-6-benzyl-4,5,6,7-tetrahydrothieno[2,3-c]
pyridin-3-yl)-furan-2-yl-methanone The procedure of Example 1 was followed except that 2-acetylfuran (Aldrich) was used in place of acetophenone to prepare the corresponding 2-(2-furanoyl)acetonitrile (Steps A and B). 1-Benzyl-4-piperidone (van der Klein et al, (1999) *J. Med. Chem.* 42: 3629–3635), 2-(2-furanoyl)acetonitrile, morpholine, and sulfur were reacted according to the procedure of Step C, Example 1, to afford the desired compound. Yield: 62%; IR (KBr) cm$^{-1}$: 3337, 3231, 2931, 2821, 1579, 1485, 1433, 1364, 1287, 734; $^1$H NMR (CDCl$_3$): δ 2.47 (t, 2H, J=4.8 Hz), 2.61 (t, 2H, J=5.6 Hz), 3.47 (s, 2H), 3.69 (s, 2H), 6.36 (bs, 2H), 6.51 (m, 1H), 7.01 (d, 1H, J=3.4 Hz), 7.31 (m, 5H), 7.55 (s, 1H); yellow solid, mp: 112–117° C. (petroleum ether).

Example 13

(2-Amino-4,5-dimethylthiophen-3-yl)-furan-2-yl-methanone

The procedure of Example 1 was followed except that 2-acetylfuran (Aldrich) was used in place of acetophenone to prepare the corresponding 2-(2-furanoyl)acetonitrile (Steps A and B). 2-Butanone (Aldrich), 2-(2-furanoyl)acetonitrile, morpholine, and sulfur were reacted according to the procedure of Step C, Example 1, to afford the desired compound. Yield: 41%; IR (KBr) cm$^{-1}$: 3265, 1573, 1474, 1426, 1293, 1158, 1021, 750; $^1$H NMR (CDCl$_3$): δ 1.24 (s, 3H), 2.05 (s, 3H), 6.52 (bs, 2H), 7.00 (s, 1H), 7.31 (s, 1H), 7.54 (s, 1H); yellow solid, mp: 95–97° C. (petroleum ether).

Example 14

(2-Amino-4,5,6,7-tetrahydrobenzo[b]thiophen-3-yl)-benzofuran-2-yl-methanone

The procedure of Example 1 was followed except that benzofuran-2-yl methyl ketone (prepared according to the procedure of Farrar and Levine (1950), *J. Amer. Chem. Soc.,* 72: 4433–4436) was used in place of acetophenone to prepare the corresponding 2-(benzofuran-2-carbonyl)acetonitrile (Steps A and B). Cyclohexanone (Aldrich), 2-(benzofuran-2-carbonyl)acetonitrile, morpholine, and sulfur were reacted according to the procedure of Step C, Example 1, to afford the desired compound. Yield: 64%; IR (KBr) cm$^{-1}$: 3430, 2927, 1575, 1430, 752; $^1$H NMR (CDCl$_3$): δ 1.56 (m, 2H), 1.81 (m, 2H), 2.29 (t, 2H, J=5.8 Hz), 2.59 (t, 2H, J=6.2 Hz), 6.55 (bs, 2H), 7.32 (m, 2H), 7.42 (t, 1H, J=7.8 Hz), 7.58 (d, 1H, J=8.2 Hz), 7.69 (d, 1H, J=7.6 Hz); yellow solid, mp: 86–89° C. (petroleum ether).

Example 15

(2-Amino-5,6-dihydro-4H-cyclopenta[b]thiophen-3-yl)-benzofuran-2-yl-methanone

The procedure of Example 1 was followed except that benzofuran-2-yl methyl ketone (Farrar and Levine (1950), *J. Amer. Chem. Soc.,* 72: 4433–4436) was used in place of acetophenone to prepare the corresponding 2-(benzofuran-2-carbonyl)acetonitrile (Steps A and B). Cyclopentanone (Aldrich), 2-(benzofuran-2-carbonyl)acetonitrile, morpholine, and sulfur were reacted according to the procedure of Step C, Example 1, to afford the desired compound. Yield: 67%; IR (KBr) cm$^{-1}$: 3298, 1570, 1540, 1422, 1288, 1257, 1156, 1034, 884, 751; $^1$H NMR (CDCl$_3$):δ 2.33 (m, 2H), 2.74 (t, 4H, J=6.8 Hz), 7.03 (bs, 2H), 7.31 (m, 2H), 7.42 (t, 1H, J=7.2 Hz), 7.57 (d, 1H, J=8.2 Hz), 7.69 (d, 1H, J=7.6 Hz); yellow solid, mp: 126–129° C. (petroleum ether).

Example 16

(2-Amino-6-benzyl-4,5,6,7-tetrahydrothieno[2,3-c]
pyridin-3-yl)-benzofuran-2-yl-methanone The procedure of Example 1 was followed except that benzofuran-2-yl methyl ketone (Farrar and Levine (1950), *J. Amer. Chem. Soc.,* 72: 4433–4436) was used in place of acetophenone to prepare the corresponding 2-(benzofuran-2-carbonyl)acetonitrile (Steps A and B). 1-Benzyl-4-piperidone (van der Klein et al., (1999) *J. Med. Chem.* 42: 3629–3635), 2-(benzofuran-2-carbonyl)acetonitrile, morpholine, and sulfur were reacted according to the procedure of Step C, Example 1, to afford the desired compound. Yield: 59%; IR (KBr) cm$^{-1}$: 3435, 1580, 1551, 1441, 749; $^1$H NMR (CDCl$_3$):δ 2.45 (m, 2H), 2.59 (t, 2H, J=5.2 Hz), 3.48 (s, 2H), 3.69 (s, 2H), 6.64 (bs, 2H), 7.33 (m, 8H), 7.58 (d, 1H, J=8 Hz), 7.66 (d, 1H, J=7.8 Hz); yellow solid, mp: 83–87° C. (petroleum ether).

Example 17

2-Amino-5,6-dihydro-4H-cyclopenta[b]thiophen-3-yl)-pyridin-2-yl-methanone

The procedure of Example 1 was followed except that 2-acetylpyridine (Aldrich) was used in place of acetophenone to prepare the corresponding 2-(pyridin-2-carbonyl)acetonitrile (Steps A and B). Cyclopentanone (Aldrich), 2-(pyridin-2-carbonyl)acetonitrile, morpholine, and sulfur were reacted according to the procedure of Step C, Example 1, to afford the desired compound. Yield: 52%; IR (KBr) cm$^{-1}$: 3338, 2853, 1582, 1560, 1453, 1424, 1355, 1307, 1278, 1146, 998, 759, 673. $^1$H NMR (CDCl$_3$):δ 2.14 (m, 4H), 2.64 (m, 2H), 7.09 (bs, 2H), 7.36 (dd, 1H, J=8.6 and 5.2 Hz), 7.58 (d, 1H, J=7.6 Hz), 7.80 (m, 1H), 8.62 (d, 1H, J=4.6 Hz); yellow solid, mp: 143–146° C. (petroleum ether).

Example 18

(2-Amino-4,5-dimethylthiophen-3-yl)-benzofuran-2-yl-methanone

The procedure of Example 1 was followed except that benzofuran-2-yl methyl ketone (Farrar and Levine (1950), *J. Amer. Chem. Soc.,* 72: 4433–4436) was used in place of acetophenone to prepare the corresponding 2-(benzofuran-2-carbonyl)acetonitrile (Steps A and B). 2-Butanone (Aldrich), 2-(benzofuran-2-carbonyl)acetonitrile, morpholine, and sulfur were reacted according to the procedure of Step C, Example 1, to afford the desired compound. Yield: 44%; IR (KBr) cm$^{-1}$: 3305, 2922, 2852, 1574, 1434, 1257, 1159, 1111, 881, 802, 750; $^1$H NMR (CDCl$_3$):δ 1.87 (s, 3H), 2.19 (s, 3H), 6.31 (bs, 2H), 7.32 (d, 2H, J=7 Hz), 7.38 (t, 1H, J=7.4 Hz), 7.57 (d, 1H, J=8.2 Hz), 7.69 (d, 1H, J=7.4 Hz); oil.

Example 19

(2-Amino-4,5,6,7-tetrahydrobenzo[b]thiophen-3-yl)-pyridin-2-yl-methanone

The procedure of Example 1 was followed except that 2-acetylpyridine (Aldrich) was used in place of acetophenone to prepare the corresponding 2-(pyridin-2-carbonyl) acetonitrile (Steps A and B). Cyclohexanone (Aldrich), 2-(pyridin-2-carbonyl)acetonitrile, morpholine, and sulfur were reacted according to the procedure of Step C, Example 1, to afford the desired compound. Yield: 58%; IR (KBr) cm$^{-1}$: 3240, 2949, 1573, 1450, 1429, 1286, 1128, 999, 754, 676; $^1$H NMR (CDCl$_3$):δ 1.46 (m, 2H), 1.71 (m, 4H), 2.50 (t, 2H, J=6.2 Hz), 6.99 (bs, 2H), 7.37 (t, 1H, J=3 Hz), 7.57 (d, 1H, J=7.8 Hz), 7.81 (t, 1H, J=7.6 Hz), 8.62 (d, 1H, J=4.6 Hz); yellow solid, mp: 191–193° C. (petroleum ether).

Example 20

(2-Amino-6-benzyl-4,5,6,7-tetrahydrothieno[2,3-c]pyridin-3-yl)-pyridin-2-yl-methanone The procedure of Example 1 was followed except that 2-acetylpyridine (Aldrich) was used in place of acetophenone to prepare the corresponding 2-(pyridin-2-carbonyl) acetonitrile (Steps A and B). 1-Benzyl-4-piperidone (van der Klein et al., (1999) *J. Med. Chem.* 42: 3629–3635), 2-(pyridin-2-carbonyl)acetonitrile, morpholine, and sulfur were reacted according to the procedure of Step C, Example 1, to afford the desired compound. Yield: 60%; IR (KBr) cm$^{-1}$: 3368, 1578, 1442, 1361, 1299, 1130, 746, 677; $^1$H NMR (CDCl$_3$). :δ 1.89 (t, 2H, J=5.8 Hz). 2.51 (t, 2H, J=5.8 Hz), 3.41 (s, 2H), 3.62 (s, 2H), 7.07 (bs, 2H), 7.32 (m, 6H), 7.54 (d, 1H, J=7.8 Hz), 7.80 (t, 1H, J=7.6 Hz), 8.63 (d, 1H, J=4.8 Hz); yellow solid, mp: 67–71° C. (petroleum ether).

Example 21

(2-Amino-4,5-dimethylthiophen-3-yl)-pyridin-2-yl-methanone

The procedure of Example 1 was followed except that 2-acetylpyridine (Aldrich) was used in place of acetophenone to prepare the corresponding 2-(pyridin-2-carbonyl) acetonitrile (Steps A and B). 2-Butanone (Aldrich), 2-(pyridin-2-carbonyl)acetonitrile, morpholine, and sulfur were reacted according to the procedure of Step C, Example 1, to afford the desired compound. Yield: 39%; IR (KBr) cm$^{-1}$: 3233, 1565, 1436, 1418, 1279, 1114, 750, 672; $^1$H NMR (CDCl$_3$):δ 1.46 (s, 3H), 2.12 (s, 3H), 6.76 (bs, 2H), 7.37 (t, 1H, J=7.0 Hz), 7.62 (d, 1H, J=7.6 Hz), 7.81 (t, 1H, J=7.6 Hz), 8.63 (d, 1H, J=4.6 Hz); yellow solid, mp: 136–139° C. (petroleum ether).

Example 22

(2-Amino-5,6-dihydro-4H-cyclopenta[b]thiophen-3-yl)-(4-bromonaphthalen-1-yl)-methanone The procedure of Example 1 was followed except that 1-acetyl-4-bromonaphthalene (prepared according to the procedure of Dixon et al., (1981) *Can. J. Chem.* 59: 2629–2641) was used in place of acetophenone to prepare the corresponding 2-(4-bromonaphthalene-1-carbonyl)acetonitrile (Steps A and B). Cyclopentanone (Aldrich), 2-(4-bromonaphthalene-1-carbonyl)acetonitrile, mor-pholine, and sulfur were reacted according to the procedure of Step C, Example 1, to afford the desired compound. Yield: 67%; IR (KBr) cm$^{-1}$: 3333, 3110, 2851, 1576, 1443, 1289, 1254, 1032, 804, 780; $^1$H NMR (CDCl$_3$):δ 1.29 (m, 2H), 1.81 (t, 2H, J=6.8 Hz), 3.31 (m, 2H), 7.34 (m, 1H), 7.53 (m, 4H), 7.71 (m, 1H), 7.95 (m, 1H), 8.64 (m, 1H); yellow solid, mp: 210–212° C. (petroleum ether).

Example 23

(2-Amino-5,6-dihydro-4H-cyclopenta[b]thiophen-3-yl)-(4-methoxynaphthalen-1-yl)-methanone The procedure of Example 1 was followed except that 1-acetyl-4-methoxynaphthalene (prepared according to the procedure of Dixon et al, (1981) *Can. J. Chem.* 59: 2629–2641) was used in place of acetophenone to prepare the corresponding 2-(4-methoxynaphthalene-1-carbonyl)acetonitrile (Steps A and B). Cyclopentanone (Aldrich), 2-(4-methoxynaphthalene-1-carbonyl)acetonitrile, mor-pholine, and sulfur were reacted according to the procedure of Step C, Example 1, to afford the desired compound. Yield: 71%; IR (KBr) cm$^{-1}$: 3351, 3243, 2852, 1581, 1433, 1261, 1242, 1162, 1091, 1023, 822, 762, 712; $^1$H NMR (CDCl$_3$):δ 1.59 (m, 2H), 1.96 (m, 2H), 2.59 (t, 2H, J=7.6 Hz), 4.04 (s, 3H), 6.79 (d, 1H, J=8 Hz), 7.12 (bs, 2H), 7.34 (d, 1H, J=8 Hz), 7.48 (m, 2H), 7.89 (m, 1H), 8.30 (m, 1H); brown solid, mp: 214–215° C. (petroleum ether).

Example 24

(2-Amino-1,6-dihydro-4H-cyclopenta[b]thiophen-3-yl)-(4-iodonaphthalen-1-yl)-methanone The procedure of Example 1 was followed except that 1-acetyl-4-iodonaphthalene (prepared according to the procedure of Dixon et al., (1981) *Can. J. Chem.* 59: 2629–2641) was used in place of acetophenone to prepare the corresponding 2-(4-iodonapthalene-1-carbonyl)acetonitrile (Steps A and B). Cyclopentanone (Aldrich), 2-(4-iodonapthalene-1-carbonyl)acetonitrile, morpholine, and sulfur were reacted according to the procedure of Step C, Example 1, to afford the desired compound. Yield: 68%; IR (KBr) cm$^{-1}$: 3329, 3221, 3106, 2852, 1581, 1444, 1290, 1254, 780; $^1$H NMR (CDCl$_3$):δ 1.28 (m, 2H), 1.81 (t, 2H, J=7 Hz), 3.34 (m, 2H), 7.36 (d, 1H, J=6.8 Hz), 7.54 (m, 2H), 7.66 (d, 1H, J=9.0 Hz), 7.97 (d, 2H, J=8.6 Hz), 8.65 (bs, 2H); yellow solid, mp: 253–255° C. (petroleum ether).

Example 25

(2-Amino-5,6-dihydro-4H-cyclopenta[b]thiophen-3-yl)-(4-chloronaph-thalen-1-yl)-methanone The procedure of Example 1 was followed except that 1-acetyl-4-chloronaphthalene (prepared according to the procedure of Dixon et al, (1981) *Can. J. Chem.* 59: 2629–2641) was used in place of acetophenone to prepare the corresponding 2-(4-chloronapthalene-1-carbonyl)acetonitrile (Steps A and B). Cyclopentanone (Aldrich), 2-(4-chloronapthalene-1-carbonyl)acetonitrile, morpholine, and sulfur were reacted according to the procedure of Step C, Example 1, to afford the desired compound. Yield: 71%; IR

Example 26

(2-Amino-4,5,6,7-tetrahydrobenzo[b]thiophen-3-yl)-(4-iodonaphthalen-1-yl)-methanone The procedure of Example 1 was followed except that 1-acetyl-4-iodonaphthalene (Dixon et al, (1981) *Can. J Chem.* 59: 2629–2641) was used in place of acetophenone to prepare the corresponding 2-(4-iodonapthalene-1-carbonyl)acetonitrile (Steps A and B). Cyclohexanone (Aldrich), 2-(4-iodonapthalene-1-carbonyl)acetonitrile, morpholine, and sulfur were reacted according to the procedure of Step C, Example 1, to afford the desired compound. Yield: 69%; IR (KBr) cm$^{-1}$: 3336, 3234, 3123, 2933, 1579, 1558, 1429, 1290, 1254, 1130, 780; $^1$H NMR (CDCl$_3$):δ 1.28 (m, 4H), 1.59 (t, 2H, J=6.4 Hz), 2.42 (t, 2H, J=6.2 Hz), 7.26 (m, 2H), 7.49 (m, 3H), 8.87 (m, 3H); yellow solid, mp: 180–182° C. (petroleum ether).

Example 27

(2-Amino-4,5,6,7-tetrahydrobenzo[b]thiophen-3-yl)-(4-methoxynaph-thalen-1-yl)-methanone The procedure of Example 1 was followed except that 1-acetyl-4-methoxynaphthalene (Dixon et a., (1981) *Can. J. Chem.* 59: 2629–2641) was used in place of acetophenone to prepare the corresponding 2-(4-methoxynapthalene-1-carbonyl)acetonitrile (Steps A and B). Cyclohexanone (Aldrich), 2-(4-iodonapthalene-1-carbonyl)acetonitrile, morpholine, and sulfur were reacted according to the procedure of Step C, Example 1, to afford the desired compound. Yield: 66%; IR (KBr) cm$^{-1}$: 3383, 3275, 2928, 1578, 1436, 1323, 1245, 1093, 733; $^1$H NMR (CDCl$_3$):δ 1.28 (m, 4H), 1.48 (t, 2H, J=7.4 Hz), 2.35 (t, 2H, J=6 Hz), 3.98 (s, 3H), 6.78 (d, 1H, J=8 Hz), 7.21 (d, 1H, J=8 Hz), 7.40 (m, 2H), 7.79 (m, 1H), 8.19 (m, 3H); yellow solid, mp: 227–229° C. (petroleum ether).

Example 28

(2-Amino-4,5,6,7-tetrahydrobenzo[b]thiophen-3-yl)-(4-chloronaphthalen-1-yl)-methanone The procedure of Example 1 was followed except that 1-acetyl-4-chloronaphthalene (Dixon et al., (1981) *Can. J. Chem.* 59: 2629–2641) was used in place of acetophenone to prepare the corresponding 2-(4-chloronapthalene-1-carbonyl)acetonitrile (Steps A and B). Cyclohexanone (Aldrich), 2-(4-chloronapthalene-1-carbonyl)acetonitrile, morpholine, and sulfur were reacted according to the procedure of Step C, Example 1, to afford the desired compound. Yield: 68%; IR (KBr) cm$^{-1}$: 3356, 3253, 2928, 1573, 1428, 1286, 1254, 1132, 941, 787, 760; $^1$H NMR (CDCl$_3$):δ 1.31 (m, 4H), 1.60 (t, 2H, J=6.4 Hz), 2.41 (t, 2H, J=6.4 Hz), 7.29 (m, 3H), 7.56 (m, 3H), 7.91 (d, 1H, J=8 Hz), 8.31 (d, 1H, J=6.8 Hz); yellow solid, mp: 179–181° C. (petroleum ether).

Example 29

(2-Amino-4,5,6,7-tetrahydrobenzo[b]thiophen-3-yl)-(4-bromonaphthalen-1-yl)-methanone The procedure of Example 1 was followed except that 1-acetyl-4-bromonaphthalene (Dixon et al., (1981) *Can. J Chem.* 59: 2629–2641) was used in place of acetophenone to prepare the corresponding 2-(4-bromonaphthalene-1-carbonyl)acetonitrile (Steps A and B). Cyclohexanone (Aldrich), 2-(4-bromonapthalene-1-carbonyl)acetonitrile, morpholine, and sulfur were reacted according to the procedure of Step C, Example 1, to afford the desired compound. Yield: 69%; IR (KBr) cm$^{-1}$: 3336, 3234, 2932, 1579, 1558, 1427, 1290, 1253, 1129, 780; $^1$H NMR (CDCl$_3$):δ 1.29 (m, 4H), 1.59 (t, 2H, J=6 Hz), 2.44 (t, 2H, J=6 Hz), 7.26 (m, 2H), 7.48 (m, 3H), 7.89 (m, 3H); yellow solid, mp: 176–178° C. (petroleum ether).

Example 30

(2-Amino-4,5,6,7-tetrahydrobenzo[b]thiophen-3-yl)-naphthalen-2-yl-methanone

The procedure of Example 1 was followed except that 2'-acetonaphthone (Aldrich) was used in place of acetophenone to prepare the corresponding 2-(napthalene-2-carbonyl)acetonitrile (Steps A and B). Cyclohexanone (Aldrich), 2-(napthalene-2-carbonyl)acetonitrile, morpholine, and sulfur were reacted according to the procedure of Step C, Example 1, to afford the desired compound. Yield: 78%; IR (KBr) cm$^{-1}$: 3392, 2929, 1560, 1424, 1292, 1128, 783; $^1$H NMR (CDCl$_3$):δ 1.43 (m, 4H), 1.75 (m, 2H), 2.53 (t, 2H, J=6.2 Hz), 7.53 (m, 3H), 7.62 (d, 1H, J=8.4 Hz), 7.89 (m, 5H); yellow solid, mp: 95–97° C. (petroleum ether).

Example 31

(2-Amino-5,6-dihydro-4 H-cyclopenta[b]thiophen-3-yl)-naphthalen-2-yl-methanone

The procedure of Example 1 was followed except that 2'-acetonaphthone (Aldrich) was used in place of acetophenone to prepare the corresponding 2-(napthalene-2-carbonyl)acetonitrile (Steps A and B). Cyclopentanone (Aldrich), 2-(napthalene-2-carbonyl)acetonitrile, morpholine, and sulfur were reacted according to the procedure of Step C, Example 1, to afford the desired compound. Yield: 67%; IR (KBr) cm$^{-1}$: 3341, 3240, 2926, 1561, 1436, 1285, 1039, 760, 742; $^1$H NMR (CDCl$_3$):δ 1.60 (m, 2H), 2.09 (m, 2H), 2.68 (m, 2H), 6.96 (bs, 2H), 7.53 (t, 2H, J=4.4 Hz), 7.60 (d, 1H, J=6.4 Hz), 7.89 (m, 4H); yellow solid, mp: 178–180° C. (petroleum ether).

Example 32

(2-Amino-6-benzyl-4,5,6,7-tetrahydrothieno[2,3-c]pyridin-3-yl)-naphthalen-2-yl-methanone The procedure of Example 1 was followed except that 2'-acetonaphthone (Aldrich) was used in place of acetophenone to prepare the corresponding 2-(napthalene-2-carbonyl)acetonitrile (Steps A and B). 1-Benzyl-4-piperidone (van der Klein et al., (1999) *J. Med. Chem.* 42: 3629–3635), 2-(napthalene-2-carbonyl)acetonitrile, morpholine, and sulfur were reacted according to the procedure of Step C, Example 1, to afford the desired compound. Yield: 78%; IR (KBr) cm$^{-1}$: 3415, 3313, 2926, 1578, 1458, 1407, 1358, 1128, 749; $^1$H NMR (CDCl$_3$):δ 1.94,(t, 2H, J=5.2 Hz), 2.41 (t, 2H, J=5.8 Hz), 3.42 (s, 2H), 3.60 (s, 2H), 6.79 (bs, 2H), 7.31 (m, 4H), 7.53 (m, 2H), 7.62 (dd, 1H, J=9.6 and 1.4 Hz), 7.87 (m, 5H); yellow solid, mp: 174–177° C. (petroleum ether).

Example 33

(2-Amino-4,5-dimethylthiophen-3-yl)-naphthalen-2-yl-methanone

The procedure of Example 1 was followed except that 2'-acetonaphthone (Aldrich) was used in place of acetophenone to prepare the corresponding 2-(napthalene-2-carbonyl)acetonitrile (Steps A and B). 2-Butanone (Aldrich), 2-(napthalene-2-carbonyl)acetonitrile, morpholine, and sulfur were reacted according to the procedure of Step C, Example 1, to afford the desired compound. Yield: 42%; IR (KBr) cm$^{-1}$: 3391, 2922, 1560, 1424, 1263, 1154, 782, 761; $^1$H NMR (CDCl$_3$):δ 1.55 (s, 3H), 2.16 (s, 3H), 6.42 (bs, 2H), 7.54 (m, 2H), 7.68 (m, 1H), 7.82 (d, 1H, J=8.4 Hz), 7.87 (m, 3H); oil.

Example 34

(2-Amino-6-spiro(1,4-dioxolan-2-yl)-4,5,6,7-tetrahydrobenzo[b]thiophen-3-yl)-(4-chlorophenyl)-methanone The procedure of Example 1 was followed except that 4-chloroacetophenone (Aldrich) was used in place of acetophenone to prepare the corresponding 2-(4-chlorobenzoyl)acetonitrile (Steps A and B). 1,4-Cyclohexanedione-mono-ethylene ketal (Aldrich), 2-(4-chlorobenzoyl)acetonitrile, morpholine, and sulfur were reacted according to the procedure of Step C, Example 1, to afford the desired compound. Yield: 78%; IR (KBr) cm$^{-1}$: 3423, 3297, 1575, 1442, 1426, 1285, 1112, 1058, 949, 839, 678; $^1$H NMR (CDCl$_3$):δ 1.66 (t, 2H, J=6.4 Hz), 2.00 (t, 2H, J=6.2 Hz), 2.74 (s, 2H), 3.99 (m, 4H), 6.77 (bs, 2H), 7.41 (m, 4H); pale yellow solid, mp: 191–193° C. (petroleum ether).

Example 35

(2-Amino-5,6-dihydro-4H-cyclopenta[b]thiophen-3-yl)-thiophen-2-yl-methanone

The procedure of Example 1 was followed except that 2-acetylthiophene (Aldrich) was used in place of acetophenone to prepare the corresponding 2-(thiophene-2-carbonyl)acetonitrile (Steps A and B). Cyclopentanone (Aldrich), 2-(thiophene-2-carbonyl)acetonitrile, morpholine, and sulfur were reacted according to the procedure of Step C, Example 1, to afford the desired compound. Yield: 67%; IR (KBr) cm$^{-1}$: 3344, 3242, 3130, 1566, 1435, 1264, 1031, 771, 747; $^1$H NMR (CDCl$_3$):δ 2.27 (m, 2H), 2.47 (t, 2H, J=7.4 Hz), 2.70 (t, 2H, J=7 Hz), 6.65 (bs, 2H), 7.06 (dd, 1H, J=3.8 and 4.8 Hz), 7.37 (dd, 1H, J=1.0 and 4.6 Hz), 7.53 (dd, 1H, J=5.0 and 1.2 Hz); yellow solid, mp: 133–134° C. (petroleum ether).

Example 36

(2-Amino-4,5-dimethylthiophen-3-yl)-thiophen-2-yl-methanone

The procedure of Example 1 was followed except that 2-acetylthiophene (Aldrich) was used in place of acetophenone to prepare the corresponding 2-(thiophene-2-carbonyl)acetonitrile (Steps A and B). 2-Butanone (Aldrich), 2-(thiophene-2-carbonyl)acetonitrile, morpholine, and sulfur were reacted according to the procedure of Step C, Example 1, to afford the desired compound. Yield: 44%; IR (KBr) cm$^{-1}$: 3390, 3269, 1552, 1429, 1272, 852, 772; $^1$H NMR (CDCl$_3$):δ 1.86 (s, 3H), 2.17 (s, 3H), 5.78(bs, 2H), 7.07 (dd, 1H, J=3.8 and 4.8 Hz), 7.56 (dd, 1H, J=2.8 and 0.8 Hz), 7.58 (dd, 1H, J=5.0 and 0.8 Hz); orange solid, mp: 117–118° C. (petroleum ether).

Example 37

(2-Amino-6-hydroxy-4,5,6,7-tetrahydrobenzo[b]thiophen-3-yl)-(4-chlorophenyl)-methanone The procedure of Example 1 was followed except that 4-chloroacetophenone (Aldrich) was used in place of acetophenone to prepare the corresponding 2-(4-chlorobenzoyl)acetonitrile (Steps A and B). 4-Hydroxycyclohexanone (prepared according to the procedure of Suzuki, Noyori, and Hamanaka, (1981) *J. Amer. Chem. Soc.* 103: 5606–5607), 2-(4-chlorobenzoyl)acetonitrile, morpholine, and sulfur were reacted according to the procedure of Step C, Example 1, to afford the desired compound. Yield: 56%; IR (KBr) cm$^{-1}$: 3354, 3242, 3146, 2912, 1573, 1557, 1426, 1294, 1074, 773; $^1$H NMR (CDCl$_3$):δ 1.80 (m, 4H), 2.50 (dd, 1H, J=12 and 4.8 Hz), 2.85 (dd, 1H, J=12 and 4.8 Hz), 4.20 (bs, 1H), 6.74 (bs, 2H), 7.40 (m, 4H); pale yellow solid, mp: 176–177° C. (petroleum ether).

Example 38

(2-Amino-6-benzyl-4,5,6,7-tetrahydrothieno[2,3-c]pyridin-3-yl)-thiophen-2-yl-methanone The procedure of Example 1 was followed except that 2-acetylthiophene (Aldrich) was used in place of acetophenone to prepare the corresponding 2-(thiophene-2-carbonyl)acetonitrile (Steps A and B). 1-Benzyl-4-piperidone (van der Klein et al., (1999), *J. Med. Chem.* 42: 3629–3635), 2-(thiophene-2-carbonyl)acetonitrile, morpholine, and sulfur were reacted according to the procedure of Step C, Example 1, to afford the desired compound. Yield: 78%; IR (KBr) cm$^{-1}$: 3412, 2928, 1570, 1419, 1355, 1265, 1119, 700; $^1$H NMR (CDCl$_3$):δ 2.35 (t, 2H, J=5.2 Hz), 2.59 (t, 2H, J=5.6 Hz), 3.47 (s, 2H), 3.67 (s, 2H), 6.26 (bs, 2H), 7.05 (m, 1H), 7.30 (d, 1H, J=5.2 Hz), 7.35 (m, 5H), 7.53 (d, 1H, J=4 Hz); yellow solid, mp: 122–123° C. (petroleum ether).

Example 39

(2-Amino-4,5,6,7-tetrahydrobenzo[b]thiophen-3-yl)-(5-bromothiophen-2-yl)-methanone The procedure of Example 1 was followed except that 2-acetyl-5-bromothiophene (Aldrich) was used in place of acetophenone to prepare the corresponding 2-(5-bromothiophene-2-carbonyl)acetonitrile (Steps A and B). Cyclohexanone (Aldrich), 2-(5-bromothiophene-2-carbonyl)acetonitrile, morpholine, and sulfur were reacted according to the procedure of Step C, Example 1, to afford the desired compound. Yield: 66%; IR (KBr) cm$^{-1}$: 3379, 3247, 2918, 1577, 1548, 1432, 1416, 1273, 761; $^1$H NMR (CDCl$_3$):δ 1.63 (m, 2H), 1.79 (m, 2H), 2.24 (t, 2H, J=5.8 Hz), 2.55 (t, 2H, J=5.8 Hz), 6.11 (bs, 2H), 7.02 (d, 1H, J=4 Hz), 7.13 (d, 1H, J=4 Hz); orange solid, mp: 160–163° C. (petroleum ether).

Example 40

(2-Amino-5,6-dihydro-4 H-cyclopenta[b]thiophen-3-yl)-(5-bromothio-phen-2-yl)-methanone The procedure of Example 1 was followed except that 2-acetyl-5-bromothiophene (Aldrich) was used in place of acetophenone to prepare the corresponding 2-(5-bromothiophene-2-carbonyl)acetonitrile (Steps A and B). Cyclopentanone (Aldrich), 2-(5-bromothiophene-2-carbonyl)acetonitrile, morpholine, and sulfur were reacted according to the procedure of Step C, Example 1, to afford the desired compound. Yield: 73%; IR (KBr) cm$^{-1}$: 3349, 3236, 3130, 1590, 1549, 1431, 1414, 1269, 975; $^1$H NMR (CDCl$_3$):δ 2.285 (m, 2H), 2.51 (t, 2H, J=7.4 Hz), 2.70 (t, 2H, J=7.4 Hz), 6.64 (bs, 2H), 7.02 (d, 1H, J=4 Hz), 7.13 (d, 1H, J=4 Hz); red solid, mp: 154–156° C. (petroleum ether).

Example 41

(2-Amino-4,5-dimethylthiophen-3-yl)-(5-bromothiophen-2-yl)-methanone

The procedure of Example 1 was followed except that 2-acetyl-5-bromothiophene (Aldrich) was used in place of acetophenone to prepare the corresponding 2-(5-bromothiophene-2-carbonyl)acetonitrile (Steps A and B). 2-Butanone (Aldrich), 2-(5-bromothiophene-2-carbonyl)acetonitrile, morpholine, and sulfur were reacted according to the procedure of Step C, Example 1, to afford the desired compound. Yield: 51%; IR (KBr) cm$^{-1}$: 3348, 1559, 1448, 1413, 1388, 1318, 1263, 974, 769; $^1$H NMR (CDCl$_3$):δ 2.16 (s, 6H), 5.90 (bs, 2H), 7.02 (d, J=4 Hz, 1H), 7.11 (d, 1H, J=4 Hz); orange solid, mp: 128–130° C. (petroleum ether).

Example 42

(2-Amino-6-benzyl-4,5,6,7-tetrahydrothieno[2,3-c]pyridin-3-yl)-(5-bromothiophen-2-yl)-methanone The procedure of Example 1 was followed except that 2-acetyl-5-bromothiophene (Aldrich) was used in place of acetophenone to prepare the corresponding 2-(5-bromothiophene-2-carbonyl)acetonitrile (Steps A and B). 1-Benzyl-4-piperidone (van der Klein et al., (1999), *J. Med. Chem.* 42: 3629–3635), 2-(5-bromothiophene-2-carbonyl)acetonitrile, morpholine, and sulfur were reacted according to the procedure of Step C, Example 1, to afford the desired compound. Yield: 72%; IR (KBr) cm$^{-1}$: 3411, 2923, 1570, 1411, 1314, 978; $^1$H NMR (CDCl$_3$):δ 2.38 (t, J=5.4 Hz, 2H), 2.59 (t, 2H, J=5.4 Hz), 3.48 (s, 2H), 3.67 (s, 2H), 6.28 (bs, 2H), 7.01 (d, 1H, J=4 Hz), 7.15 (d, 1H, J=4 Hz), 7.32 (m, 5H); brown solid, mp: 87–89° C. (petroleum ether).

Example 43

(2-Amino-4,5,6,7-tetrahydrobenzo[b]thiophen-3-yl)-(5-chlorothiophen-2-yl)-methanone The procedure of Example 1 was followed except that 2-acetyl-5-chlorothiophene (Aldrich) was used in place of acetophenone to prepare the corresponding 2-(5-chlorothiophene-2-carbonyl)acetonitrile (Steps A and B). Cyclohexanone (Aldrich), 2-(5-chlorothiophene-2-carbonyl)acetonitrile, morpholine, and sulfur were reacted according to the procedure of Step C, Example 1, to afford the desired compound. Yield: 76%; IR (KBr) cm$^{-1}$: 3349, 3237, 3131, 2911, 1577, 1547, 1430, 1281, 1006, 765; $^1$H NMR (CDCl$_3$):δ 1.59 (m, 2H), 1.65 (m, 2H), 2.35 (t, 2H, J=5.8 Hz), 2.55 (t, 2H, J=5.8 Hz), 6.07 (bs, 2H), 6.88 (d, 1H, J=4 Hz), 7.16 (d, 1H, J=4 Hz); yellow solid, mp: 173–175° C. (petroleum ether).

Example 44

(2-Amino-5,6-dihydrocyclopenta[b]thiophen-3-yl)-(5-chlorothiophen-2-yl)-methanone The procedure of Example 1 was followed except that 2-acetyl-5-chlorothiophene (Aldrich) was used in place of acetophenone to prepare the corresponding 2-(5-chlorothiophene-2-carbonyl)acetonitrile (Steps A and B). Cyclopentanone (Aldrich), 2-(5-chlorothiophene-2-carbonyl)acetonitrile, morpholine, and sulfur were reacted according to the procedure of Step C, Example 1, to afford the desired compound. Yield: 69%; IR (KBr) cm$^{-1}$: 3351, 3244, 3132, 2851, 1590, 1550, 1426, 1270, 1002, 813, 698; $^1$H NMR (CDCl$_3$): δ 2.28 (m, 2H), 2.52 (t, 2H, J=7.2 Hz), 2.70 (t, 2H, J=7.2 Hz), 6.62 (bs, 2H), 6.88 (d, 1H, J=4 Hz), 7.16 (d, 1H, J=4 Hz); red solid, mp: 170–171° C. (petroleum ether).

Example 45

(2-Amino-4,5-dimethylthiophen-3-yl)-(5-chlorothiophen-2-yl)-methanone

The procedure of Example 1 was followed except that 2-acetyl-5-chlorothiophene (Aldrich) was used in place of acetophenone to prepare the corresponding 2-(5-chlorothiophene-2-carbonyl)acetonitrile (Steps A and B). 2-Butanone (Aldrich), 2-(5-chlorothiophene-2-carbonyl)acetonitrile, morpholine, and sulfur were reacted according to the procedure of Step C, Example 1, to afford the desired compound. Yield: 46%; IR (KBr) cm$^{-1}$: 3377, 3259, 2918, 1551, 1424, 1326, 1266, 1003, 764; $^1$H NMR (CDCl$_3$):δ 1.90 (s, 3H), 2.17 (s, 3H), 5.77 (bs, 2H), 6.89 (d, 1H, J=4 Hz), 7.16 (d, 1H, J=4 Hz); red solid, mp: 125–127° C. (petroleum ether).

Example 46

(2-Amino-6-benzyl-4,5,6,7-tetrahydrothieno[2,3-c]pyridin-3-yl)-(5-chlorothiophen-2-yl)-methanone The procedure of Example 1 was followed except that 2-acetyl-5-chlorothiophene (Aldrich) was used in place of acetophenone to prepare the corresponding 2-(5-chlorothiophene-2-carbonyl)acetonitrile (Steps A and B). 1-Benzyl-4-piperidone (van der Klein et al., (1999) *J. Med. Chem.* 42: 3629–3635), 2-(5-chlorothiophene-2-carbonyl)acetonitrile, morpholine, and sulfur were reacted according to the procedure of Step C, Example 1, to afford the desired compound. Yield: 63%; IR (KBr) cm$^{-1}$: 3306, 2956, 2807, 1715, 1574, 1428, 1354, 1122, 1008, 742, 699; $^1$H NMR (CDCl$_3$):δ 2.39 (m, 2H), 2.59 (t, 2H, J=5.2 Hz), 3.45 (s, 2H), 3.67 (s, 2H), 6.26 (bs, 2H), 6.87 (d, 1H, J=3.8 Hz), 7.19 (d, 1H, J=4 Hz), 7.35 (m, 5H); yellow solid, mp: 81–83° C. (petroleum ether).

Example 47

(2-Amino-4,5,6,7-tetrahydrobenzo[b]thiophen-3-yl)-thiophen-3-yl-methanone

The procedure of Example 1 was followed except that 3-acetylthiophene (Aldrich) was used in place of acetophenone to prepare the corresponding 2-(thiophene-3-carbonyl) acetonitrile (Steps A and B). Cyclohexanone (Aldrich), 2-(thiophene-3-carbonyl)acetonitrile, morpholine, and sulfur were reacted according to the procedure of Step C, Example 1, to afford the desired compound. Yield: 67%; IR (KBr) cm$^{-1}$: 3323, 3107, 2929, 1576, 1433, 1266, 1151, 1080, 825,726; $^1$H NMR (CDCl$_3$):δ 1.55 (m, 2H), 1.77 (m, 2H), 2.01 (t, 2H, J=6 Hz), 2.54 (t, 2H, J=6.2 Hz), 6.46 (bs, 2H), 7.28 (m, 2H), 7.58 (t, 1H, J=2.2 Hz); yellow solid, mp: 133–135° C. (petroleum ether).

Example 48

(2-Amino-5,6-dihydro-4H-cyclopenta[b]thiophen-3-yl)-thiophen-3-yl-methanone

The procedure of Example 1 was followed except that 3-acetylthiophene (Aldrich) was used in place of acetophenone to prepare the corresponding-2-(thiophene-3-carbonyl) acetonitrile (Steps A and B). Cyclopentanone (Aldrich), 2-(thiophene-3-carbonyl)acetonitrile, morpholine, and sulfur were reacted according to the procedure of Step C, Example 1, to afford the desired compound. Yield: 71%; IR (KBr) cm$^{-1}$: 3330, 3117, 2846, 1569, 1448, 1435, 1265, 855, 836, 757, 715; $^1$H NMR (CDCl$_3$):δ 2.24 (m, 4H), 2.71 (m, 2H), 6.83 (bs, 2H), 7.33 (m, 2H), 7.56 (m, 1H); yellow solid, mp: 125–127° C. (petroleum ether).

Example 49

(2-Amino-4,5-dimethylthiophen-3-yl)-thiophen-3-yl-methanone

The procedure of Example 1 was followed except that 3-acetylthiophene (Aldrich) was used in place of acetophenone to prepare the corresponding 2-(thiophene-3-carbonyl) acetonitrile (Steps A and B). 2-Butanone (Aldrich), 2-(thiophene-3-carbonyl)acetonitrile, morpholine, and sulfur were reacted according to the procedure of Step C, Example 1, to afford the desired compound. Yield: 38%; IR (KBr) cm$^{-1}$: 3337, 3229, 3107, 1576, 1427, 1265, 1162, 855, 736, 719; $^1$H NMR (CDCl$_3$):δ 1.71 (s, 3H), 2.15 (s, 3H), 6.17 (bs, 2H), 7.30 (d, J=2.2 Hz, 2H), 7.63 (t, 1H, J=2 Hz); yellow solid, mp: 122–123° C. (petroleum ether).

Example 50

(2-Amino-6-benzyl-4,5,6,7-tetrahydrothieno[2,3-c]pyridin-3-yl)-thiophen-3-yl-methanone The procedure of Example 1 was followed except that 3-acetyl-thiophene (Aldrich) was used in place of acetophenone to prepare the corresponding 2-(thiophene-3-carbonyl) acetonitrile (Steps A and B). 1-Benzyl-4-piperidone (van der Klein et al., (1999) *J. Med. Chem.* 42: 3629–3635), 2-(thiophene-3-carbonyl)acetonitrile, morpholine, and sulfur were reacted according to the procedure of Step C, Example 1, to afford the desired compound. Yield: 68%; IR (KBr) cm$^{-1}$: 3350, 3234, 2805, 1578, 1524, 1429, 1257, 1147, 984, 856, 799, 722; $^1$H NMR (CDCl$_3$):δ 2.14 (m, 2H), 2.54 (t, 2H, J=5.6 Hz), 3.43 (s, 2H), 3.65 (s, 2H), 6.61 (bs, 2H), 7.33 (m, 7H), 7.58 (m, 1H); yellow solid, mp: 131–133° C. (petroleum ether).

Example 51

[2-Amino-6-(4-methoxyphenyl)-4H-1,5,7-trithia-inden-3-yl]-napthalen-1-yl-methanone The procedure of Example 1 was followed except that 1'-acetonaphthone (Aldrich) was used in place of acetophenone to prepare the corresponding 2-(naphthalene-1-carbonyl)acetonitrile (Steps A and B). 2-(4-Methoxyphenyl)-1,3-dithian-5-one (prepared according to the procedure of Luettringhaus, Mohr, and Englehard, *J. Liebig's Ann. Chem.* (1963) 661: 84–94), 2-(naphthalene-1-carbonyl)-acetonitrile, morpho-line, and sulfur were reacted according to the procedure of Step C, Example 1, to afford the desired compound. Yield: 77%; IR (KBr) cm$^{-1}$: 3412, 1607, 1578, 1509, 1420, 1303, 1254, 1176, 1112, 1029, 778; $^1$H NMR (CDCl$_3$):δ 2.17 (s, 2H), 3.77 (s, 3H), 3.81 (s, 1H), 6.78 (d, 2H, J=8.6 Hz), 7.28 (bs, 2H), 7.29 (m, 2H), 7.51 (m, 5H), 7.93 (m, 2H); yellow solid, mp: 132–134° C. (petroleum ether).

Example 52

[2-Amino-6-(4-methoxyphenyl)-4H-1,5,7-trithia-inden-3-yl]-(4-chlorophenyl)-methanone The procedure of Example 1 was followed except that 4-chloroacetophenone (Aldrich) was used in place of acetophenone to prepare the corresponding 2-(4-chlorobenzoyl)acetonitrile (Steps A and B). 2-(4-Methoxyphenyl)-1,3-dithian-5-one (Luettringhaus, Mohr, and Englehard, *J. Liebig's Ann. Chem.* (1963) 661: 84–94), 2-(4-chlorobenzoyl)acetonitrile, morpholine, and sulfur were reacted according to the procedure of Step C, Example 1, to afford the desired compound. Yield: 74%; IR (KBr) cm$^{-1}$: 3436, 3311, 1607, 1578, 1509, 1432, 1255, 1174, 1090, 1025, 838; $^1$H NMR (CDCl$_3$) δ 3.29 (d, 2H, J=6.8 Hz), 3.80 (s, 3H), 3.82 (s, 1H), 6.65 (bs, 2H), 6.88 (t, 2H, J=8.6 Hz), 7.35 (d, 2H, J=8.6 Hz), 7.40 (d, 2H, J=8.4 Hz), 7.57 (d, 2H, J=8.4 Hz); yellow solid, mp: 158–160° C. (petroleum ether).

Example 53

[2-Amino-6-(4-methoxyphenyl)-4H-1,5,7-trithia-inden-3-yl]-thiophen-2-yl-methanone The procedure of Example 1 was followed except that 2-acetylthiophene (Aldrich) was used in place of acetophenone to prepare the corresponding 2-(thiophene-2-carbonyl) acetonitrile (Steps A and B). 2-(4-Methoxyphenyl)-1,3-dithian-5-one (Luettringhaus, Mohr, and Englehard, *J. Liebig's Ann. Chem.* (1963) 661: 84–94), 2-(thiophene-2-carbonyl)acetonitrile, morpholine, and sulfur were reacted according to the procedure of Step C, Example 1, to afford the desired compound. Yield: 75%; IR (KBr) cm$^{-1}$: 3429, 3324, 1608, 1566, 1509, 1436, 1254, 1174, 1029, 838, 716; $^1$H NMR (CDCl$_3$):δ 3.69 (d, 2H, J=6.8 Hz), 3.81 (s, 3H), 3.83 (s, 1H), 6.14 (bs, 2H), 6.87 (t, 2H, J=8.8 Hz), 7.11 (m, 1H), 7.38 (d, 2H, J=8.8 Hz), 7.56 (d, 1H, J=3.2 Hz), 7.62 (d, 1H, J=5 Hz); orange solid, mp: 138–140° C. (petroleum ether).

Example 54

(2-Amino-4,5,6,7-tetrahydrobenzo[b]thiophen-3-yl)-(9H-fluorene-2-yl)-methanone

The procedure of Example 1 was followed except that 2-acetylfluorene (Aldrich) was used in place of acetophenone to prepare the corresponding 2-(fluorene-2-carbonyl)acetonitrile (Steps A and B). Cyclohexanone (Aldrich), 2-(fluorene-2-carbonyl)acetonitrile, morpholine, and sulfur were reacted according to the procedure of Step C, Example 1, to afford the desired compound. Yield: 66%; IR (KBr) cm$^{-1}$: 3428, 2927, 1560, 1431, 1267, 1228, 1139, 760; $^1$H NMR (CDCl$_3$):δ 1.48 (m, 2H), 1.72 (m, 2H), 1.86 (t, 2H, J=6 Hz), 2.53 (t, 2H, J=6 Hz), 3.94 (s, 2H), 6.53 (bs, 2H), 7.37 (m, 2H), 7.55 (t, 1H, J=7.2 Hz), 7.70 (s, 2H), 7.81 (t, 2H, J=7.8 Hz); yellow solid, mp: 146–149° C. (petroleum ether).

Example 55

(2-Amino-5,6-dihydro-4H-cyclopenta[b]thiophen-3-yl)-(9H-fluoren-2-yl)-methanone

The procedure of Example 1 was followed except that 2-acetylfluorene (Aldrich) was used in place of acetophenone to prepare the corresponding 2-(fluorene-2-carbonyl)acetonitrile (Steps A and B). Cyclopentanone (Aldrich), 2-(fluorene-2-carbonyl)acetonitrile, morpholine, and sulfur were reacted according to the procedure of Step C, Example 1, to afford the desired compound. Yield: 68%; IR (KBr) cm$^{-1}$: 3400, 2928, 2846, 1685, 1560, 1430, 1268, 737; $^1$H NMR (CDCl$_3$):δ 2.15 (m, 4H), 2.69 (m, 2H), 3.94 (s, 2H), 6.86 (bs, 2H), 7.36 (m, 3H), 7.54 (d, 1H, J=8 Hz), 7.58 (d, 1H, J=7.8 Hz), 7.89 (t, 2H, J=7.8 Hz); yellow solid, mp: 176–182° C. (petroleum ether).

Example 56

(2-Amino-6-benzyl-4,5,6,7-tetrahydrothieno[2,3-c]pyridin-3-yl)-(9H-fluoren-2-yl)-methanone The procedure of Example 1 was followed except that 2-acetylfluorene (Aldrich) was used in place of acetophenone to prepare the corresponding 2-(fluorene-2-carbonyl)acetonitrile (Steps A and B). 1-Benzyl-4-piperidone (van der Klein et al, (1999) J. Med. Chem. 42: 3629–3635), 2-(fluorene-2-carbonyl)acetonitrile, morpholine, and sulfur were reacted according to the procedure of Step C, Example 1, to afford the desired compound. Yield: 73%; IR (KBr) cm$^{-1}$: 3410, 3311, 1602, 1578, 1471, 1355, 1264, 1230, 1123, 764, 748, 699; $^1$H NMR (CDCl$_3$):δ 2.00 (t, 2H, J=5.2 Hz), 2.46 (t, 2H, J=5 Hz), 3.44 (s, 2H), 3.61 (s, 2H), 3.94 (s, 2H), 6.68 (bs, 2H), 7.32 (m, 7H), 7.55 (t, 2H, J=7.6 Hz), 7.69 (s, 1H), 7.79 (d, 2H, J=7.6 Hz); yellow solid, mp: 197–200° C. (petroleum ether).

Example 57

[2-Amino-6-[(methanesulfonyl)oxy]-4,5,6,7-tetrahydrobenzo[b]thiophen-3-yl]-(4-chlorophenyl)-methanone The procedure of Example 1 was followed except that 4-chloroacetophenone (Aldrich) was used in place of acetophenone to prepare the corresponding 2-(4-chlorobenzoyl)acetonitrile (Steps A and B). 4-(Methanesulfonyloxy)cyclo-hexanone (prepared according to the procedure of Yadav and Jeyaraj, (1998) J. Org. Chem. 63: 3474–3477), 2-(4-chlorobenzoyl)acetonitrile, morpholine, and sulfur were reacted according to the procedure of Step C, Example 1, to afford the desired compound. Yield: 56%; IR (KBr) cm$^{-1}$: 3429, 2928, 1577, 1432, 1349, 1172, 944; $^1$H NMR (CDCl$_3$): 1.88 (t, 2H, J=6.2 Hz), 1.97 (t, 2H, J=4.8 Hz), 2.94 (m, 2H), 3.03 (s, 3H), 5.07 (m, 1H), 6.75 (bs, 2H), 7.41 (m, 4H); yellow solid, mp: 73–75° C. (petroleum ether).

Example 58

[2-Amino-6-(4-chlorobenzyl)-4,5,6,7-tetrahydrothieno[2,3-c]pyridin-3-yl]-naphthalen-2-yl-methanone The procedure of Example 1 was followed except that 2'-acetonaphthone (Aldrich) was used in place of acetophenone to prepare the corresponding 2-(naphthalene-2-carbonyl)acetonitrile (Steps A and B). 1-(4-Chlorobenzyl)-4-piperidone (prepared according to the procedure of van der Klein et al., (1999) J. Med. Chem. 42: 3629–3635), 2-(naphthalene-2-carbonyl)acetonitrile, morpholine, and sulfur were reacted according to the procedure of Step C, Example 1, to afford the desired compound. Yield: 68%; IR (KBr) cm$^{-1}$: 3392, 2963, 1715, 1577, 1423, 1262, 1088, 1016, 800; $^1$H NMR (CDCl$_3$):δ 1.93 (t, 2H, J=5.6 Hz), 2.43 (t, 2H, J=5.8 Hz), 3.42 (s, 2H), 3.56 (s, 2H), 6.80 (bs, 2H), 7.26 (s, 4H), 7.59 (m, 3H), 7.92 (m, 4H); mp: 105–108° C. (petroleum ether).

Example 59

2-Amino-6-(4-fluorobenzyl)-4,5,6,7-tetrahydrothieno[2,3-c]pyridin-3-yl]-naphthalen-2-yl-methanone The procedure of Example 1 was followed except that 2'-acetonaphthone (Aldrich) was used in place of acetophenone to prepare the corresponding 2-(naphthalene-2-carbonyl)acetonitrile (Steps A and B). 1-(4-Fluorobenzyl)-4-piperidone (prepared according to the procedure of van der Klein et al., (1999) J. Med. Chem. 42: 3629–3635), 2-(naphthalene-2-carbonyl)acetonitrile, morpholine, and sulfur were reacted according to the procedure of Step C, Example 1, to afford the desired compound. Yield: 69%; IR (KBr) cm$^{-1}$: 3401, 2928, 1577, 1508, 1424, 1263, 1221, 1130, 824; $^1$H NMR (CDCl$_3$):δ 1.96 (t, 2H, J=5.4 Hz), 2.38 (t, 2H, J=5.6 Hz), 3.42 (s, 2H), 3.56 (s, 2H), 6.81 (bs, 2H), 6.98 (t, 2H, J=8.8 Hz), 7.27 (t, 2H, J=6.2 Hz), 7.56 (m, 2H), 7.90 (m, 5H); mp: 94–96° C. (petroleum ether).

Example 60

(2-Amino-6-benzyl-4,5,6,7-tetrahydrobenzo[b]thiophen-3-yl)-naphthalen-2-yl-methanone

The procedure of Example 1 was followed except that 2'-acetonaphthone (Aldrich) was used in place of acetophenone to prepare the corresponding 2-(naphthalene-2-carbonyl)acetonitrile (Steps A and B). 4-Benzyl-cyclohexanone (prepared according to the procedure of Rosowsky et al., (1999) *J. Med. Chem.* 42: 1007–1017), 2-(naphthalene-2-carbonyl)acetonitrile, morpholine, and sulfur were reacted according to the procedure of Step C, Example 1, to afford the desired compound. Yield: 61%; IR (KBr) cm$^{-1}$: 3369, 2914, 1569, 1424, 1285, 1252, 782; $^1$H NMR (CDCl$_3$) δ 1.17 (m, 2H), 1.27 (m, 1H), 1.56 (m, 1H), 1.81 (m, 1H), 2.19 (m, 2H), 2.49 (d, 2H, J=7 Hz), 7.03 (bs, 2H), 7.29 (m, 6H), 7.48 (m, 5H), 7.88 (d, 1H, J=8.8 Hz); mp: 69–70° C. (petroleum ether).

Example 61

[2-Amino-6-(2-fluorobenzyl)-4,5,6,7-tetrahydrothieno[2,3-c]pyridin-3-yl]-naphthalen-2-yl-methanone

The procedure of Example 1 was followed except that 2'-acetonaphthone (Aldrich) was used in place of acetophenone to prepare the corresponding 2-(naphthalene-2-carbonyl)acetonitrile (Steps A and B). 1-(2-Fluorobenzyl)-4-piperidone (prepared according to the procedure of van der Klein et al., (1999) *J. Med. Chem.* 42: 3629–3635), 2-(naphthalene-2-carbonyl)acetonitrile, morpholine, and sulfur were reacted according to the procedure of Step C, Example 1, to afford the desired compound. Yield: 70%; IR (KBr) cm$^{-1}$: 3420, 3316, 2793, 1579, 1458, 1358, 1285, 1228, 1131, 762; $^1$H NMR (CDCl$_3$):δ 1.95 (t, 2H, J=5.6 Hz), 2.45 (t, 2H, J=5.4 Hz), 3.49 (s, 2H), 3.66 (s, 2H), 6.61 (bs, 2H), 7.08 (m, 3H), 7.31 (m, 1H), 7.35 (d, 1H, J=7.2 Hz), 7.54 (t, 2H, J=4.2 Hz), 7.63 (d, 1H, J=8.6 Hz), 7.86 (m, 2H), 7.97 (s, 1H); mp: 183–185° C. (petroleum ether).

Example 62

[2-Amino-6-(2-chlorobenzyl)-4,5,6,7-tetrahydrothieno[2,3-c]pyridin-3-yl]-naphthalen-2-yl-methanone

The procedure of Example 1 was followed except that 2'-acetonaphthone (Aldrich) was used in place of acetophenone to prepare the corresponding 2-(naphthalene-2-carbonyl)acetonitrile (Steps A and B). 1-(2-Chlorobenzyl)-4-piperidone (prepared according to the procedure of van der Klein et al., (1999) *J. Med. Chem.* 42: 3629–3635), 2-(naphthalene-2-carbonyl)acetonitrile, morpholine, and sulfur were reacted according to the procedure of Step C, Example 1, to afford the desired compound. Yield: 68%; IR (KBr) cm$^{-1}$: 3419, 3317, 2918, 2792, 1600, 1578, 1461, 1410, 1359, 1282, 1135, 984, 781, 759; $^1$H NMR (CDCl$_3$):δ 1.96 (t, 2H, J=5.4 Hz), 2.49 (t, 2H, J=5.6 Hz), 3.53 (s, 2H), 3.73 (s, 2H), 6.60 (bs, 2H), 7.19 (m, 4H), 7.46 (d, 1H, J=6.6 Hz), 7.52 (t, 2H, J=6.4 Hz), 7.61 (d, 1H, J=8.4 Hz), 7.88 (m, 2H), 7.99 (s, 1H); mp: 169–171° C. (petroleum ether).

Example 63

[2-Amino-6-(3,4,5-trimethoxybenzyl)-4,5,6,7-tetrahydrothieno[2,3-c]pyri-din-3-yl]-naphthalen-2-yl-methanone

The procedure of Example 1 was followed except that 2'-acetonaphthone (Aldrich) was used in place of acetophenone to prepare the corresponding 2-(naphthalene-2-carbonyl)acetonitrile (Steps A and B). 1-(3,4,5-Trimethoxybenzyl)-4-piperidone (prepared according to the procedure of van der Klein et al., (1999) *J. Med. Chem.* 42: 3629–3635), 2-(naphthalene-2-carbonyl)-acetonitrile, morpholine, and sulfur were reacted according to the procedure of Step C, Example 1, to afford the desired compound. Yield: 89%; IR (KBr) cm$^{-1}$: 3394, 2933, 2831, 1578, 1421, 1358, 1233, 1125, 1005, 782; $^1$H NMR (CDCl$_3$):δ 1.93 (t, 2H, J=5.6 Hz), 2.40 (t, 2H, J=5.6 Hz), 3.46 (s, 2H), 3.52 (s, 2H), 3.81 (s, 3H), 3.83 (s, 6H), 6.53 (s, 2H), 6.62 (bs, 2H), 7.53 (t, 2H, J=4 Hz), 7.62 (d, 1H, J=8.8 Hz), 7.87 (m, 3H), 7.98 (s, 1H); mp: 127–129° C. (petroleum ether).

Example 64

(2-Amino-6-benzyl-4,5,6,7-tetrahydrobenzo[b]thiophen-3-yl)-thiophen-2-yl-methanone

The procedure of Example 1 was followed except that 2-acetylthiophene (Aldrich) was used in place of acetophenone to prepare the corresponding 2-(thiophen-2-carbonyl)acetonitrile (Steps A and B). 4-Benzyl-cyclohexanone (Rosowsky et al., (1999) *J. Med. Chem.* 42: 1007–1017), 2-(thiophen-2-carbonyl)acetonitrile, morpholine, and sulfur were reacted according to the procedure of Step C, Example 1, to afford the desired compound. Yield: 72%; IR (KBr) cm$^{-1}$: 3465, 2925, 1554, 1425, 1270, 1041, 768, 730, 702; $^1$H NMR (CDCl$_3$):⊏ 0.88 (m, 1H), 1.27 (m, 2H, 1.56 (m, 1H), 2.23 (m, 3H), 2.66 (dd, 2H, J=7.2 and 3 Hz), 6.11 (bs, 2H), 7.04 (t,1H, J=4.4 Hz), 7.23 (m, 6H), 7.52 (d, 1H, J=4.8 Hz); mp: 116–118° C. (petroleum ether).

Example 65

(2-Amino-6-benzyl-4,5,6,7-tetrahydrobenzo[b]thiophen-3-yl)-thiophen-3-yl-methanone

The procedure of Example 1 was followed except that 3-acetylthiophene (Aldrich) was used in place of acetophenone to prepare the corresponding 2-(thiophen-3-carbonyl)acetonitrile (Steps A and B). 4-Benzyl-cyclohexanone (Rosowsky et al., (1999) *J. Med. Chem.* 42: 1007–1017), 2-(thiophen-3-carbonyl)acetonitrile, morpholine, and sulfur were reacted according to the procedure of Step C, Example 1, to afford the desired compound. Yield: 65%; IR (KBr) cm$^{-1}$: 3401, 2920, 1560, 1547, 1419, 1260, 700; $^1$H NMR (CDCl$_3$):δ 0.79 (m, 1H), 1.29 (m, 2H), 1.49 (m, 1H), 2.17 (m, 3H), 2.66 (m, 2H), 7.02 (bs, 2H), 7.28 (m, 8H); mp: 57–58° C. (petroleum ether).

Example 66

(2-Amino-6-benzyl-4,5,6,7-tetrahydrobenzo[b]thiophen-3-yl)-(4-chlorophenyl)-methanone

The procedure of Example 1 was followed except that 4-chloroacetophenone (Aldrich) was used in place of acetophenone to prepare the corresponding 2-(4-chlorobenzoyl)acetonitrile (Steps A and B). 4-Benzylcyciohexanone (Rosowsky et al., (1999) *J. Med. Chem.* 42: 1007–1017), 2-(4-chlorobenzoyl)acetonitrile, morpholine, and sulfur were reacted according to the procedure of Step C, Example 1, to afford the desired compound. Yield: 63%; IR (KBr) cm$^{-1}$: 3435, 2923, 1577, 1430, 1088, 700; $^1$H NMR (CDCl$_3$):δ 0.88 (m, 1H), 1.28 (m, 2H), 1.72 (m, 1H), 2.25 (m, 3H), 2.59 (d, 2H, J=7 Hz), 6.70 (bs, 2H), 7.26 (m, 9H); mp: 60–62° C. (petroleum ether).

Example 67

(2-Amino-6-benzyl-4,5,6,7-tetrahydrobenzo[b]thiophen-3-yl]-naphthalen-2-yl-methanone The procedure of Example 1 was followed except that 2'-acetonaphthone (Aldrich) was used in place of acetophenone to prepare the corresponding 2-(naphthalene-2-carbonyl)acetonitrile (Steps A and B). 4-Benzyl-cyclohexanone (Rosowsky et al., (1999) *J. Med. Chem.* 42: 1007–1017), 2-(naphthalene-2-carbonyl)-acetonitrile, morpholine, and sulfur were reacted according to the procedure of Step C, Example 1, to afford the desired compound. Yield: 60%; IR (kBr) cm$^{-1}$: 3419, 3315, 2912, 1596, 1568, 1456, 1282, 1130, 781, 749, 699; $^1$H NMR (CDCl$_3$):δ 1.04 (m, 2H), 1.62, (m, 2H), 1.81 (m, 1H), 2.19 (m, 2H), 2.59 (d, 2H, J=7.4 Hz), 6.67 (bs, 2H), 7.19 (m, 4H), 7.56 (m, 4H), 7.88 (m, 4H): mp: 153° C. (petroleum ether).

Example 68

[2-Amino-6-(4-nitrobenzyl)-4,5,6,7-tetrahydrobenzo[b]thiophen-3-yl]-naphthalen-2-yl-methanone The procedure of Example 1 was followed except that 2'-acetonaphthone (Aldrich) was used in place of acetophenone to prepare the corresponding 2-(naphthalene-2-carbonyl)acetonitrile (Steps A and B). 1-(4-Nitrobenzyl)-4-piperidone (van der Klein et al, (1999) *J. Med. Chem.* 42: 3629–3635), 2-(naphthalene-2-carbonyl)-acetonitrile, morpholine, and sulfur were reacted according to the procedure of Step C, Example 1, to afford the desired compound. Yield: 68%; IR (KBr) cm$^{-1}$: 3422, 1577, 1518, 1424, 1344, 858, 740; $^1$H NMR (CDCl$_3$):δ 1.94 (t, 2H, J=5.4 Hz), 2.42 (t, 2H, J=5.4 Hz), 3.45 (s, 2H), 3.68 (s, 2H), 6.80 (bs, 2H), 7.58 (m, 5H), 7.91 (m, 4H), 8.15 (d, 2H, J=8.6 Hz); mp: 76–78° C. (petroleum ether).

Example 69

Pharmaceutical Formulations

| (A) Transdermal System - for 1000 patches | |
|---|---|
| Ingredients | Amount |
| Active compound | 100 g |
| Silicone fluid | 450 g |
| Colloidal silicon dioxide | 2 g |

The silicone fluid and active compound are mixed together and the colloidal silicone dioxide is added to increase viscosity. The material is then dosed into a subsequent heat sealed polymeric laminate comprised of the following: polyester release liner, skin contact adhesive composed of silicone or acrylic polymers, a control membrane which is a polyolefin, and an impermeable backing membrane made of a polyester multilaminate. The resulting laminated sheet is than cut into 10 sq. cm patches

| (B) Oral Tablet - For 1000 Tablets | |
|---|---|
| Ingredients | Amount |
| Active compound | 50 g |
| Starch | 50 g |
| Magnesium Stearate | 5 g |

The active compound and the starch are granulated with water and dried. Magnesium stearate is added to the dried granules and the mixture is thoroughly blended. The blended mixture is compressed into tablets.

| (C) Injection - for 1000, 1 mL Ampules | |
|---|---|
| Ingredients | Amount |
| Active compound | 10 g |
| Buffering Agents | q.s. |
| Propylene glycol | 400 mg |
| Water for injection | q.s. 1000 mL |

The active compound and buffering agents are dissolved in the propylene glycol at about 50° C. The water for injection is then added with stirring and the resulting solution is filtered, filled into ampules, sealed and sterilized by autoclaving.

| (D) Continuous Injection - for 1000 mL | |
|---|---|
| Ingredients | Amount |
| Active compound | 10 g |
| Buffering agents | q.s. |
| Water for injection | q.s. 1000 mL |

Those skilled in the art will recognize, or be able to ascertain using no more than routine experimentation, many equivalents, modifications and variations to the specific embodiments of the invention described herein. For example, other excipients may be utilized in preparing the pharmaceutical formulations. In addition, some of the compounds described herein contain one or more asymmetric centers and may therefore give rise to enantiomers and diastereomers as well as their racemic and resolved, enantiomerically pure or diastereomerically pure forms, and pharmaceutically acceptable saltsa thereof. Moreover, it will be appreciated that the general representation of such paired variables as $R^3$ and $R^4$, in formula IA, is not to be construed as to represent a particular orientation of the paired members. Accordingly, it is not intended that the present invention be limited to the specifics of the foregoing description of the preferred embodiments and example compounds, but rather as being limited only by the scope of the invention as defined in the claims appended hereto, including enantiomeric, diastereomeric and pharmaceutical salt forms.

What is claimed is:

1. A method for providing pain management, comprising administering to a patient in need of treatment thereof an effective amount to treat the disorder of a compound of formula IA:

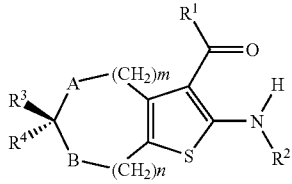
(IA)

wherein:

R¹ is

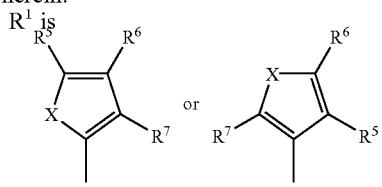

wherein R² is H, C(=O)R⁸;

R⁸ is H, alkyl, substituted alkyl, aralkyl, substituted aralkyl, aryl, or substituted aryl;

R³ and R⁴ are independently H, alkyl, substituted alkyl, aryl, substituted aryl, aralkyl, alkenyl, substituted alkenyl, alkynyl, substituted alkynyl, halogen, hydroxy, alkylsulfonyloxy, arylsulfonyloxy, substituted arylsulfonyloxy, alkoxy, alkylthio, or arylthio;

or if R³ and R⁴ are both alkoxy or alkylthio, may form a 1,3-dioxolan-2-yl, 1,3-dioxan-2-yl, 1,3-dithiolan-2-yl, or 1,3-dithian-2-yl group;

or together R³ and R⁴ may form a carbonyl oxygen; R⁵, R⁶, and R⁷ are independently H, alkyl, substituted alkyl, aryl, substituted aryl, halogen, hydroxy, nitro, amino, substituted amino, disubstituted amino, alkoxy, aryloxy, alkylthio, arylthio, sulfonamido, or substituted sulfonamido;

and wherein together R⁵ and R⁶ or R⁶ and R⁷ are CH=CH—CH=CH, such that they form a fused aromatic ring;

A and B are each a carbon-carbon single bond;

m and n are independently 0, 1, 2, or 3;

m plus n equals 3; and

X is CH=CH.

2. The method of claim 1, wherein the pain management involves the treatment of diabetic neuropathy, post herpetic neuralgia or other forms of neuropathic pain.

3. The method of claim 2 wherein the treatment involves acute intravenous injection, chronic oral administration or chronic intravenous injection.

4. The method of claim 1 wherein the compound is selected from the group consisting of:
(2-Amino-4,5,6,7-tetrahydrobenzo[b]thiophen-3-yl)-naphthalen-1-yl-methanone;
(2-Amino-4,5,6,7-tetrahydrobenzo[b]thiophen-3-yl)-(4-iodonaphthalen-1-yl)-methanone;
(2-Amino-4,5,6,7-tetrahydrobenzo[b]-thiophen-3-yl)-(4-methoxynaph-thalen-1-yl)-methanone;
(2-Amino-4,5,6,7-tetrahydrobenzo[b]thiophen-3-yl)-(4-chloronaphthalen-1-yl)-methanone;
(2-Amino-4,5,6,7-tetrahydrobenzo[b]thiophen-3-yl)-(4-bromonaphthalen-1-yl)-methanone;
(2-Amino-4,5,6,7-tetrahydrobenzo[b]thiophen-3-yl)-naphthalen-2-yl-methanone;
(2-Amino-6-benzyl-4,5,6,7-tetrahydrobenzo[b]thiophen-3-yl)-naphthalen-2-yl- methanone;
(2-Amino-6-benzyl-4,5,6,7-tetrahydrobenzo[b]thiophen-3-yl]-naphthalen-2-yl-methanone; and
[2-Amino-6-(4-nitrobenzyl)-4,5,6,7-tetrahydrobenzo[b]thiophen-3-yl]-naphthalen-2-yl-methanone.

5. The method of claim 1, wherein the compound is selected from the group consisting of:
(2-Amino-4,5,6,7-tetrahydrobenzo[b]thiophen-3-yl)-naphthalen-1-yl-methanone;
(2-Amino-4,5,6,7-tetrahydrobenzo[b]thiophen-3-yl)-(4-iodonaphthalen-1-yl)-methanone;
(2-Amino-4,5,6,7-tetrahydrobenzo[b]thiophen-3-yl)-(4-methoxynaphthalen-1-yl)-methanone;
(2-Amino-4,5,6,7-tetrahydrobenzo[b]thiophen-3-yl)-(4-chloronaphthalen-1-yl)-methanone;
(2-Amino-4,5,6,7-tetrahydrobenzo[b]thiophen-3-yl)-(4-bromonaphthalen-1-yl)-methanone; and
(2-Amino-4,5,6,7-tetrahydrobenzo[b]thiophen-3-yl)-naphthalen-2-yl-methanone.

6. The method of claim 5, wherein the compound is (2-Amino-4,5,6,7-tetrahydrobenzo[b]thiophen-3-yl)-naphthalen-1-yl-methanone.

7. The method of claim 5, wherein the compound is (2-Amino-4,5,6,7-tetrahydrobenzo[b]thiophen-3-yl)-(4-chloronaphthalen-1-yl)-methanone.

8. The method of claim 5, wherein the compound is (2-Amino-4,5,6,7-tetrahydrobenzo[b]thiophen-3-yl)-naphthalen-2-yl-methanone.

* * * * *

UNITED STATES PATENT AND TRADEMARK OFFICE
CERTIFICATE OF CORRECTION

PATENT NO. : 7,112,607 B2  Page 1 of 1
APPLICATION NO. : 10/101817
DATED : September 26, 2006
INVENTOR(S) : Pier Giovanni Baraldi It is certified that error appears in the above-identified patent and that said Letters Patent is hereby corrected as shown below:

Column 2, lines 33-55, the formula IB should appear as follows:

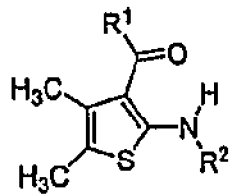

wherein:
$R^1$ is 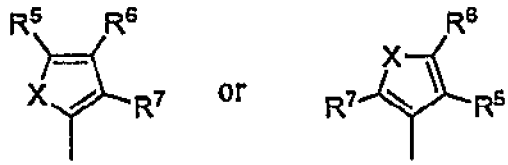

Signed and Sealed this

Thirty-first Day of July, 2007

JON W. DUDAS
*Director of the United States Patent and Trademark Office*